United States Patent
Yamaguchi et al.

(10) Patent No.: US 9,342,807 B2
(45) Date of Patent: May 17, 2016

(54) MANAGEMENT SYSTEM, COMPUTER SYSTEM, AND METHOD OF PROVIDING INFORMATION

(71) Applicant: Sysmex Corporation, Kobe-shi, Hyogo (JP)

(72) Inventors: Tadayuki Yamaguchi, Kobe (JP); Atsushi Shirakami, Miki (JP); Takeshi Matsumoto, Kasai (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 14/626,305

(22) Filed: Feb. 19, 2015

(65) Prior Publication Data

US 2015/0161552 A1    Jun. 11, 2015

Related U.S. Application Data

(63) Continuation of application No. 12/322,185, filed on Jan. 30, 2009, now Pat. No. 8,996,929.

(30) Foreign Application Priority Data

Jan. 31, 2008    (JP) ................................. 2008-020011

(51) Int. Cl.
*G06F 11/00* (2006.01)
*G06Q 10/06* (2012.01)
*G06F 19/00* (2011.01)

(52) U.S. Cl.
CPC ...... *G06Q 10/06395* (2013.01); *G06F 19/3412* (2013.01); *G06F 19/327* (2013.01)

(58) Field of Classification Search
None
See application file for complete search history.

(56) References Cited

U.S. PATENT DOCUMENTS

| | | | |
|---|---|---|---|
| 6,192,320 B1 | 2/2001 | Margrey et al. | |
| 6,748,337 B2 | 6/2004 | Wardlaw et al. | |
| 7,519,492 B2 | 4/2009 | Miller et al. | |
| 7,725,297 B2 * | 5/2010 | Okuno et al. | 702/187 |
| 2002/0128801 A1 | 9/2002 | Okuno et al. | |
| 2007/0027635 A1 | 2/2007 | Yamasaki et al. | |
| 2007/0239377 A1 | 10/2007 | Reiner | |
| 2009/0076755 A1 | 3/2009 | Yundt-Pacheco | |

FOREIGN PATENT DOCUMENTS

JP    2003-279583    10/2003

* cited by examiner

*Primary Examiner* — Yolanda L Wilson
(74) *Attorney, Agent, or Firm* — Brinks Gilson & Lione

(57) ABSTRACT

A management system includes a plurality of analyzers; and a computer system connected to the analyzers via a network, wherein each of the analyzers comprises: a data transmitter for transmitting data produced by the analyzer to the computer system via the network, and wherein the computer system includes a memory under control of a processor, the memory storing instructions enabling the processor to carry out operations, comprising: (a) receiving a plurality of data transmitted from the data transmitters of the plurality of analyzers; (b) generating an aggregate result used for determining a determination condition for making a determination as to whether or not a notification to a user of the analyzer is required based on the plurality of received data; and (c) outputting the aggregate result. A computer system and a method of providing information are also disclosed.

20 Claims, 15 Drawing Sheets

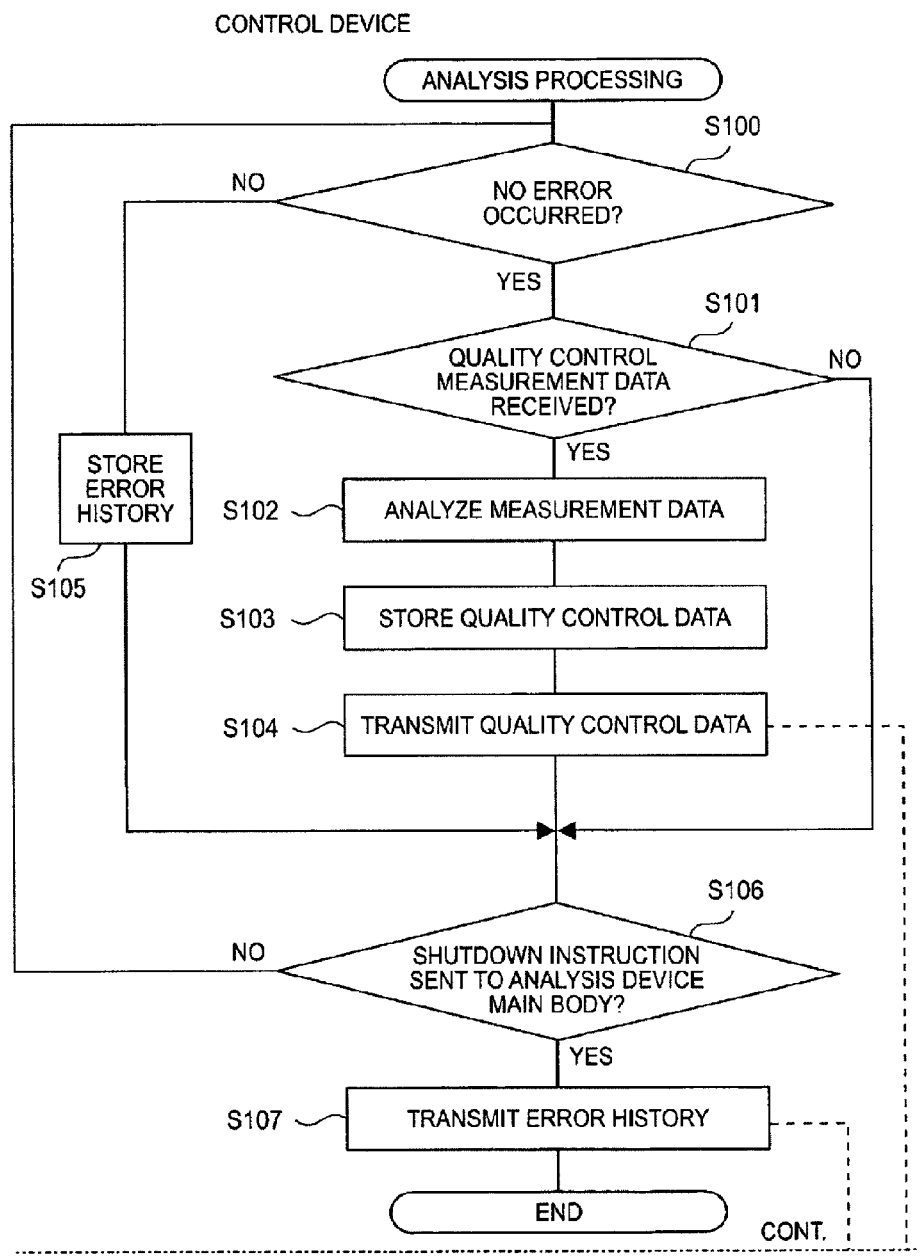

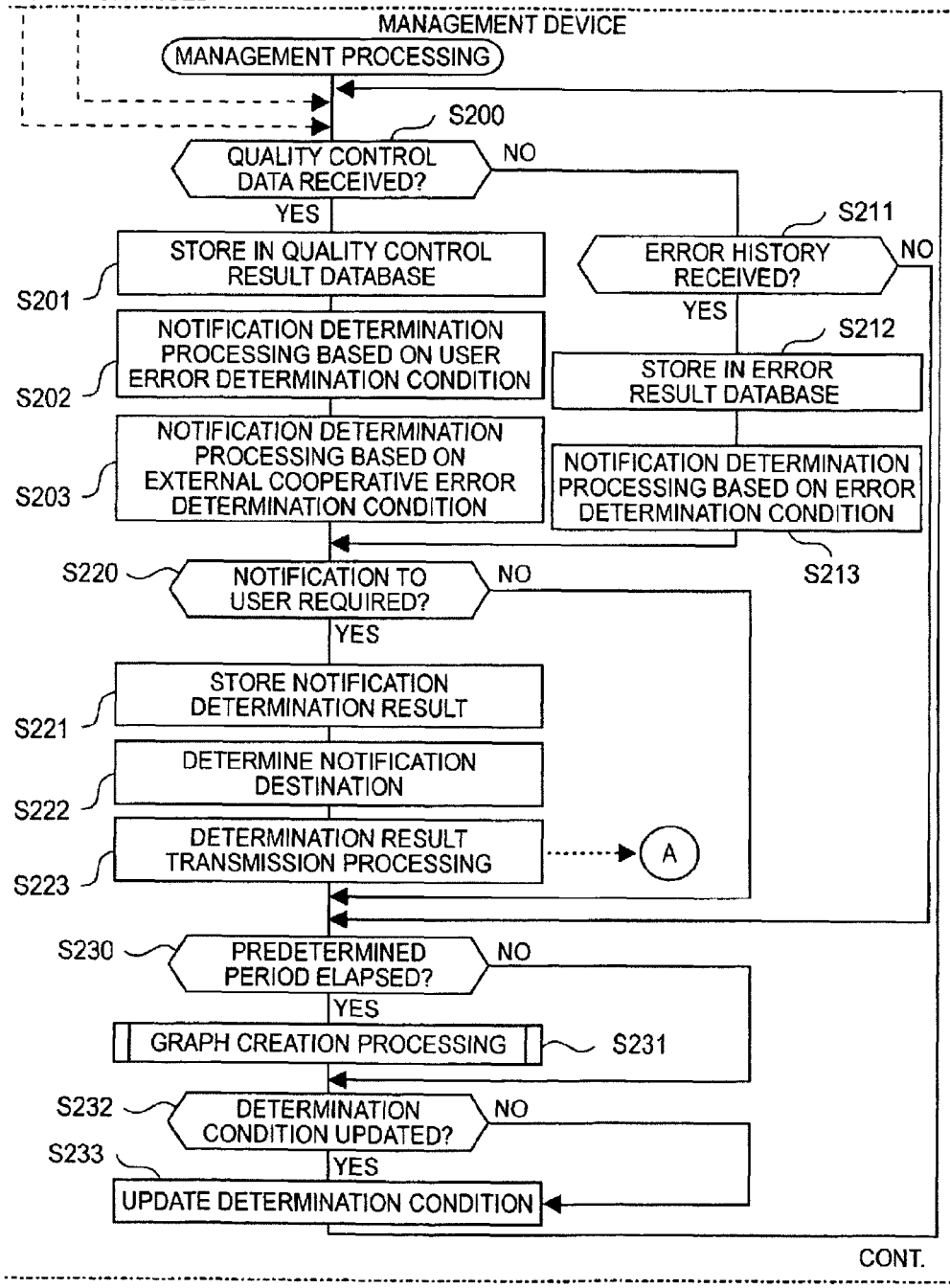

FIG.8

| | | |
|---|---|---|
| 241a | FACILITY NAME | FACILITY A |
| 241b | DEVICE NAME | DEVICE A |
| 241c | PS Code | 98313314 |
| 241d | SERIAL NO. | 11048 |
| 242a | MATERIAL NAME | QUALITY CONTROL SUBSTANCE A |
| 242b | MATERIAL LEVEL | LOW |
| 242c | Lot No. | QC-01500601 |
| 243a | DATE | 2008/01/07 |
| 243b | TIME | 09:03:09 |
| 244a | NUMBER OF ITEMS | 3 |
| 244b | RBC | 447 |
| 244c | HGB | 13.5 |
| 244d | WBC | 38.4 |

(240; 241 groups 241a–241d; 242 groups 242a–242c; 243 groups 243a–243b; 244 groups 244a–244d)

FIG.9

| MATERIAL NAME (251) | LEVEL (252) | MEASUREMENT ITEM (253) | ABNORMALITY DETERMINATION RULE (254) | USER DETERMINATION AVAILABILITY (255) | EXTERNAL COOPERATIVE ERROR DETERMINATION AVAILABILITY (256) |
|---|---|---|---|---|---|
| QUALITY CONTROL SUBSTANCE A | LOW | RBC | ACTION LIMIT OVER | YES | NO |
| | | | TREND | YES | YES |
| | | | ⋮ | ⋮ | ⋮ |
| QUALITY CONTROL SUBSTANCE B | NORMAL | HGB | ACTION LIMIT OVER | YES | YES |
| | | | TREND | YES | NO |
| | | | ⋮ | ⋮ | ⋮ |

FIG.10

QUALITY CONTROL ERROR DETERMINATION CONDITION

PLEASE SET QUALITY CONTROL ERROR DETERMINATION.

ABNORMALITY DETERMINATION CONDITION

| MATERIAL NAME | LEVEL | MEASURE-MENT ITEM | ABNORMALITY DETERMINATION RULE | USER DETERMINATION AVAILABILITY | EXTERNAL COOPERATIVE ERROR DETERMINATION AVAILABILITY |
|---|---|---|---|---|---|
| QUALITY CONTROL SUBSTANCE A | LOW | RBC | ACTION LIMIT OVER | ☑ | ☐ |
| | | | TREND | ☑ | ☑ |
| | | | : | : | : |
| | NORMAL | HGB | ACTION LIMIT OVER | ☐ | ☑ |
| | | | TREND | ☑ | ☐ |
| | | | : | : | : |
| QUALITY CONTROL SUBSTANCE B | LOW | RBC | ACTION LIMIT OVER | ☑ | ☑ |
| | | | TREND | ☑ | ☑ |
| | | | : | : | : |
| | NORMAL | HGB | ACTION LIMIT OVER | ☐ | ☐ |
| | | | TREND | ☑ | ☑ |
| | | | : | : | : |

317 — OK     CANCEL — 318

FIG.11

| FACILITY NAME | FACILITY A |
|---|---|
| DEVICE NAME | DEVICE A |
| PS Code | 98313314 |
| SERIAL NO. | 11048 |
| MATERIAL NAME | QUALITY CONTROL SUBSTANCE A |
| MATERIAL LEVEL | LOW |
| Lot No. | QC-01500601 |
| MEASUREMENT ITEM | RBC |
| ACTION LIMIT OVER | ON |
| TREND | ON |
| : | : |
| ACTION LIMIT OVER | ON |
| TREND | ON |
| : | : |
| DATE | 2008/01/07 |
| TIME | 09:03:09 |
| RBC | 447 |
| ABNORMALITY DETERMINATION RULE | ACTION LIMIT OVER |

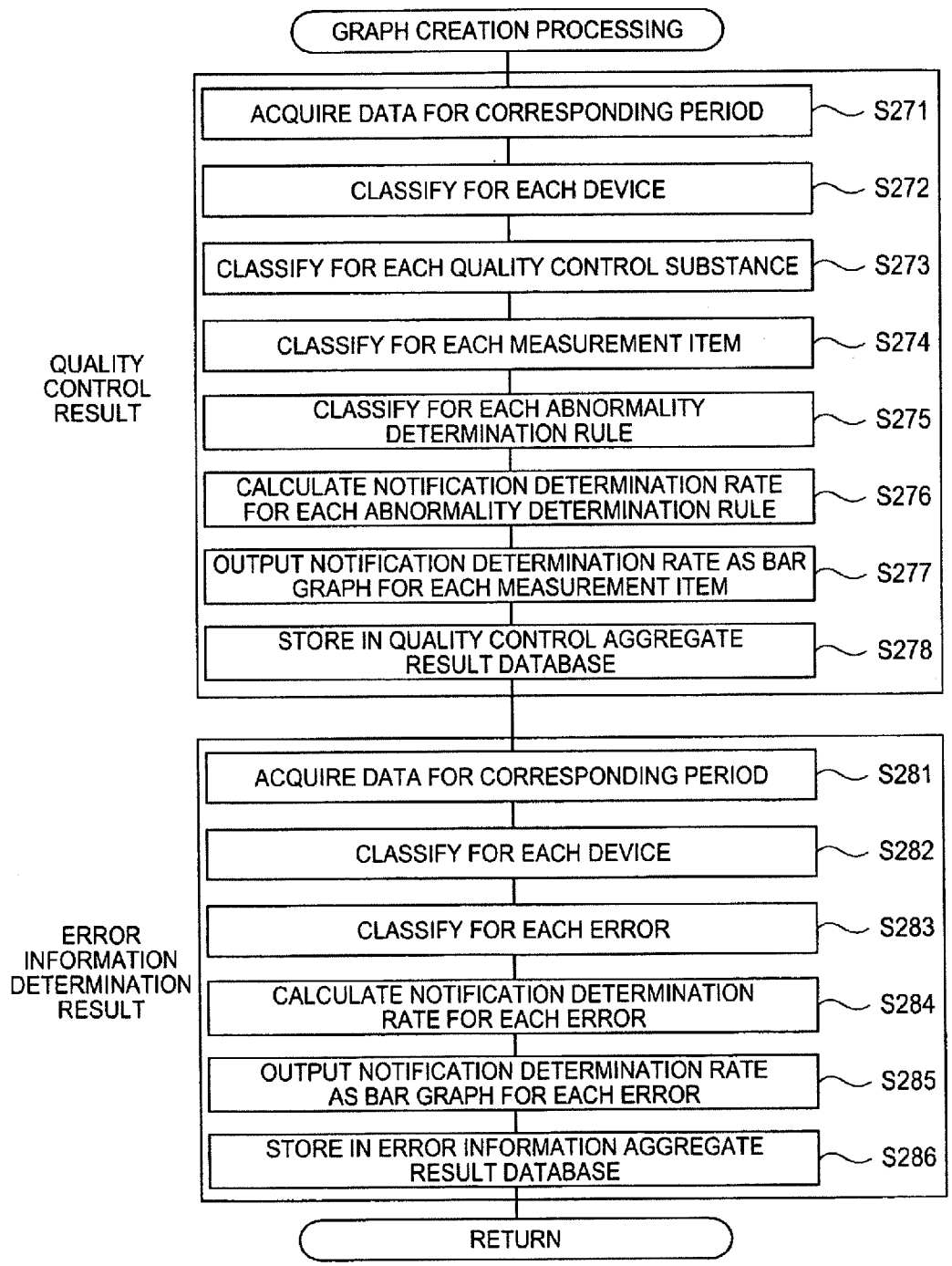

FIG.15

| SERIAL NUMBER | DEVICE INFORMATION | | | | DATE AND TIME | | ERROR CODE |
|---|---|---|---|---|---|---|---|
| | FACILITY NAME | DEVICE NAME | PS Code | SERIAL NO. | DATE | TIME | |
| 1 | FACILITY A | DEVICE A | 98313314 | 11048 | 2008/01/07 | 11:59:26 | 211000 |
| 2 | FACILITY A | DEVICE A | 98313314 | 11048 | 2008/01/07 | 13:29:28 | 161010 |

FIG.16

| DEVICE NAME | ERROR NAME | ERROR CODE | ACTION LIMIT |
|---|---|---|---|
| DEVICE A | SHORT SAMPLE | 161010 | 10 |
| | WHOLE BLOOD ASPIRATION MOTOR STOPPAGE ABNORMALITY | 211000 | 1 |
| | BLANK ERROR | 411010 | 2 |
| | RACK OPERATION ABNORMALITY | 252001 | 5 |
| | RACK ID READING ABNORMALITY | 446040 | 10 |
| | : | : | : |

FIG.17

| DEVICE INFORMATION | FACILITY NAME | FACILITY A |
|---|---|---|
| | DEVICE NAME | DEVICE A |
| | PS Code | 98313314 |
| | SERIAL NO. | 11048 |
| ERROR OCCURRENCE DATE AND TIME | OCCURRENCE DATE | 2008/01/07 |
| | OCCURRENCE TIME | 11:30:36 |
| ERROR INFORMATION | ERROR NAME | WHOLE BLOOD ASPIRATION MOTOR STOPPAGE ABNORMALITY |
| | ERROR CODE | 211000 |
| Action Limit | | 1 |

FIG. 18

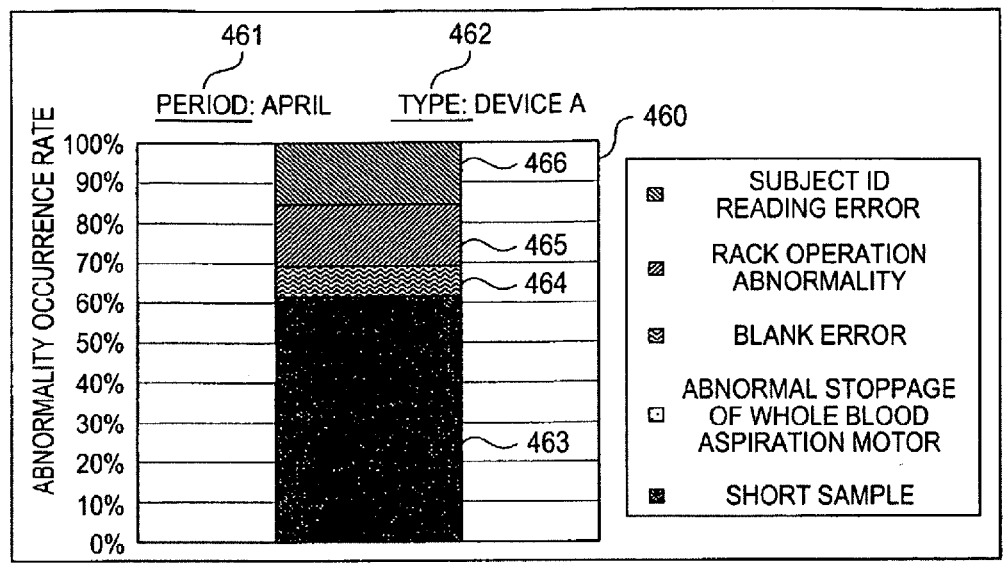

FIG. 19

| MATERIAL NAME | LEVEL | MEASUREMENT ITEM | ABNORMALITY DETERMINATION RULE | USER DETERMINATION AVAILABILITY |
|---|---|---|---|---|
| QUALITY CONTROL SUBSTANCE A | LOW | RBC | ACTION LIMIT OVER | ☑ |
| | | | TREND | ☑ |
| | | | ⋮ | ⋮ |
| | NORMAL | HGB | ACTION LIMIT OVER | ☐ |
| | | | TREND | ☑ |
| | | | ⋮ | ⋮ |
| QUALITY CONTROL SUBSTANCE B | LOW | RBC | ACTION LIMIT OVER | ☑ |
| | | | TREND | ☑ |
| | | | ⋮ | ⋮ |
| | NORMAL | HGB | ACTION LIMIT OVER | ☐ |
| | | | TREND | ☑ |
| | | | ⋮ | ⋮ |

QUALITY CONTROL ERROR DETERMINATION CONDITION
PLEASE SET USER QUALITY CONTROL ERROR DETERMINATION CONDITION.
USER DETERMINATION CONDITION

OK   CANCEL

MANAGEMENT SYSTEM, COMPUTER SYSTEM, AND METHOD OF PROVIDING INFORMATION

RELATED APPLICATIONS

This application is a continuation application of U.S. patent application Ser. No. 12/322,185 filed on Jan. 30, 2009, which claims priority to Japanese Patent Application No. 2008-020011 filed Jan. 31, 2008, the entire contents of which are hereby incorporated by reference.

FIELD OF THE INVENTION

The present invention relates to a management system having a management system connected to a plurality of analysis devices via a network, a computer system, and a method of providing information.

BACKGROUND

A remote support system is known in which a plurality of analysis devices is connected to a management device via a network. For example, U.S. Patent Application Publication No. 2002-128801 discloses a remote support system in which a management device collects quality control data obtained by measuring a quality control substance from a plurality of analysis devices and calculates an aggregate result for each analysis device and for each quality control substance. According to the remote support system disclosed in U.S. Patent Application Publication No. 2002-128801, the management device analyzes the quality control data, and when a quality control result is outside a predetermined range or when worsening of the quality control data is expected, a notification thereof is sent to a user thereof.

As described above, the remote support system of U.S. Patent Application Publication No. 2002-128801 is extremely useful because the management device is capable of detecting a trouble in the analysis device based on a predetermined setting to send a notification thereof to a user thereof, so that the trouble occurring in the analysis device can be promptly treated. However, U.S. Patent Application Publication No. 2002-128801 does not provide any suggestion as to how the settings for detecting the trouble in the analysis device can be determined. For this reason, there is a desire to obtain useful information for determining the settings. For example, when the settings are too loose, information on a trouble which is not required to be notified to a user may be notified to the user, imposing an unnecessary burden to the user. On the other hand, when the settings are too strict, information on a trouble which must have been notified to the user might not be notified to the users.

SUMMARY OF THE INVENTION

The scope of the present invention is defined solely by the appended claims, and is not affected to any degree by the statements within this summary.

A first aspect of the present invention is a management system, comprising: a plurality of analyzers; and a computer system connected to the analyzers via a network, wherein each of the analyzers comprises: a data transmitter for transmitting data produced by the analyzer to the computer system via the network, and wherein the computer system includes a memory under control of a processor, the memory storing instructions enabling the processor to carry out operations, comprising: (a) receiving a plurality of data transmitted from the data transmitters of the plurality of analyzers; (b) generating an aggregate result used for determining a determination condition for making a determination as to whether or not a notification to a user of the analyzer is required based on the plurality of received data; and (c) outputting the aggregate result.

A second aspect of the present invention is a computer system connected to a plurality of analyzers via a network, comprising: a memory under control of a processor, the memory storing instructions enabling the processor to carry out operations, wherein the instructions comprise, (a) receiving a plurality of data transmitted from the plurality of analyzers; (b) generating an aggregate result used for determining a determination condition for making a determination as to whether or not a notification to a user of the analyzer is required based on the plurality of received data; and (c) outputting the generated aggregate result.

A third aspect of the present invention is a method of providing information for determining whether or not a notification to a user is required based on data received from a plurality of analyzers, comprising: (a) receiving data transmitted from the plurality of analyzers; (b) generating an aggregate result used for determining a determination condition for making a determination as to whether or not a notification to a user of the analyzer is required based on the received data; and (c) outputting the generated aggregate result.

BRIEF DESCRIPTION OF THE DRAWINGS

FIG. 8 is a diagram illustrating an example of quality control data which are transmitted from the analysis device illustrated in FIG. 1 to the management device.

FIG. 9 is a diagram illustrating an example of a quality control error determination condition database provided to the management device illustrated in FIG. 1.

FIG. 10 is a diagram illustrating an example of a dialog screen for updating the quality control error determination condition.

FIG. 11 is a diagram illustrating an example of quality control error determination result data which are transmitted from the management device illustrated in FIG. 1 to a terminal equipment of the call center.

FIG. 12 is a flow chart illustrating an exemplary procedure of a graph creating process of the management device illustrated in FIG. 1.

FIG. 15 is a diagram illustrating an example of error information that is transmitted from the analysis device illustrated in FIG. 1 to the management device.

FIG. 16 is a diagram illustrating an example of error information determination condition database provided to the management device illustrated in FIG. 1.

FIG. 17 is a diagram illustrating an example of a device error determination result that is transmitted from the management device illustrated in FIG. 1 to the terminal equipment of the call center.

FIG. 18 is a diagram illustrating an example of a graph that is output in step S285 and displayed on the terminal equipment 300 of the call center 203.

FIG. 19 is a diagram illustrating an example of a dialog screen for updating a quality control error determination condition on an analysis device side.

DETAILED DESCRIPTION OF THE PREFERRED EMBODIMENTS

The preferred embodiments of the present invention will be described hereinafter with reference to the drawings.

First, a description of a management system according to an embodiment of the present invention will be provided in detail with reference to the drawings.

Figure 1:
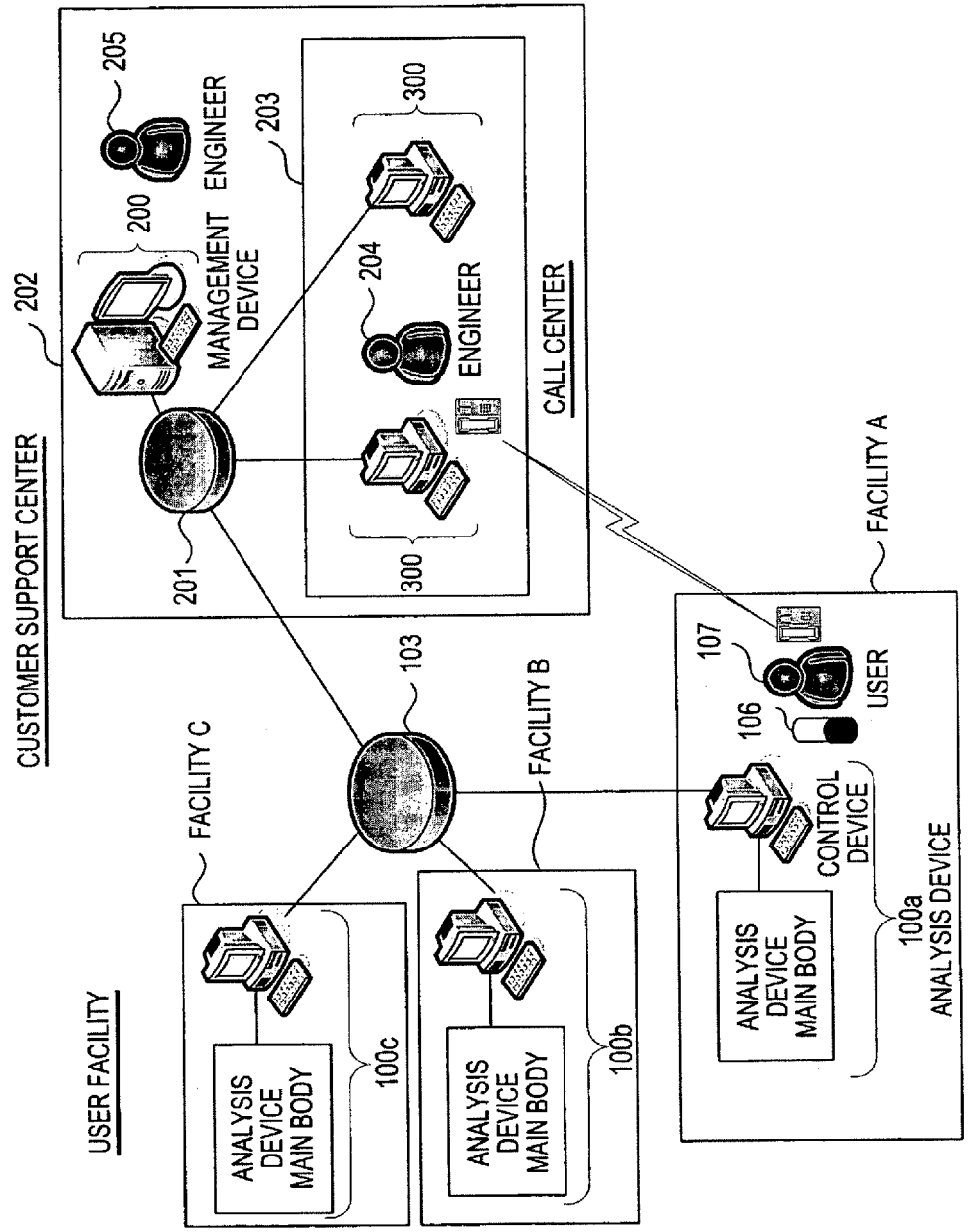
FIG. 1 is a diagram illustrating an example of an overall configuration of a management system for managing a plurality of analysis devices according to a first embodiment.

FIG. 1 is a diagram illustrating a configuration of a management system according to the embodiment. As illustrated in FIG. 1, the management system according to the present embodiment includes an analysis device 100a installed in a facility A, an analysis device 100b installed in a facility B, an analysis device 100c installed in a facility C, a network 103 such as the Internet, a management device 200 installed in a customer support center 202, a network 201 such as a LAN, and a plurality of terminal equipments 300 installed in a call center 203. It is to be noted that a plurality of analysis devices 100a, 100b, and 100c may be installed in one facility. A description of the processing to the analysis device 100a will be provided hereinbelow by way of an example.

The customer support center 202 is a facility of a vendor who provides maintenance services for the analysis device 100a and has an engineer 205 capable of operating the management device 200.

The call center 203 is a facility which is provided in the customer support center 202 to enable the engineer 204 of the call center 203 to make calls to a user 107 of the analysis device 100a to cope with failures or inquiries. The user 107 of the analysis device 100a takes a measurement of a quality control substance 106 by means of the analysis device 100a prior to a measurement of a sample of a human subject. The quality control substance 106 is a sample prepared using a human blood, as a raw material, so as to include a predetermined component in a predetermined concentration, and the e-CHECK (available from Sysmex Corporation) may be used, for example. When the quality control substance 106 is measured by the analysis device 100a, an analysis result thereof is transmitted to the management device 200 via the networks 103 and 201. When the analysis result (quality control data) of the quality control substance 106 transmitted from the analysis device 100a has exceeded a predetermined range, the management device 200 sends a notification thereof to the terminal equipment 300. When the notification from the management device 200 is received by the terminal equipment 300, the engineer 204 makes a call to the user 107 of the facility A being a sender of the analysis result and resolves a trouble occurring in the analysis device 100a.

Moreover, upon occurrence of an error during the measurement, the analysis device 100a transmits error information thereof to the management device 200 via the networks 103 and 201. When the error information satisfies a predetermined condition, the management device 200 sends a notification thereof to the terminal equipment 300. When the notification has been received by the terminal equipment 300 from the management device 200, the engineer 204 makes a call to the user 107 of the analysis device 100a being the sender of the analysis result to resolve a trouble occurring in the analysis device 100a. As the analysis device 100a, a variety of sample analysis devices are used, e.g., a biochemical analysis device, a blood cell counter, a blood coagulation measurement device, an immunological measurement device, and a urinary analysis device. The analysis device 100a to be connected to the management device 200 is not limited to one type, but a plurality of types of devices such as a combination of a biochemical analysis device and a blood cell counter may be connected to the management device. In this embodiment, a description of an example where only a blood cell counter is connected will be provided for the sake of simple description.

Figure 2:
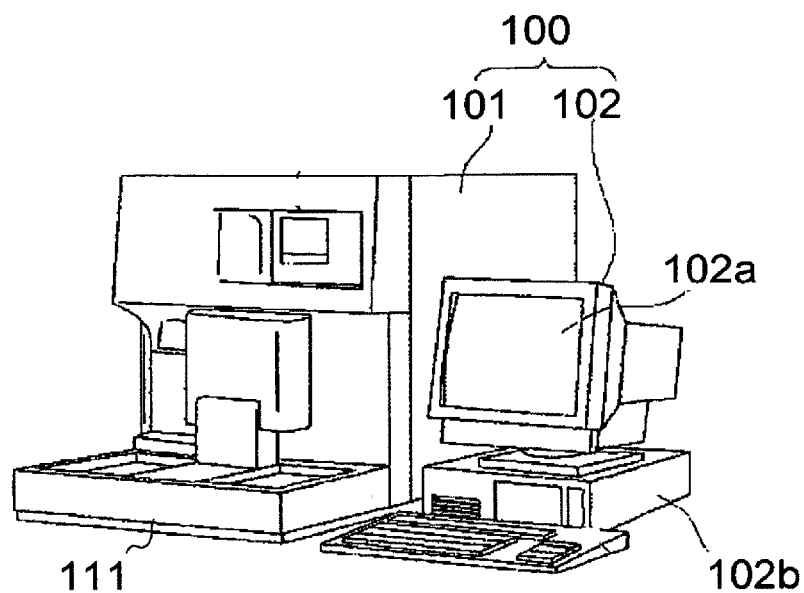
FIG. 2 is a perspective view of an analysis device illustrated in FIG. 1.

FIG. 2 is a perspective view illustrating an overall configuration of the analysis device 100a. The analysis device 100a is a blood cell counter used for a blood examination, and is configured by an analysis device main body 101 and a control device 102. The analysis device main body 101 is provided with a transfer section 111 capable of transferring a subject to an aspiratory position of the analysis device main body. For example, when the quality control substance 106 has been measured in the analysis device 100a, the analysis device main body 101 transmits measurement data to the control device 102, the measurement data being obtained by aspirating and measuring the quality control substance 106 transferred to the subject aspiratory position of the analysis device main body 101 by the transfer section 111.

The control device 102 performs an analysis on the received measurement data within a main body thereof 102b and displays the quality control data 240 (see FIG. 8) obtained through the analysis on a display 102a.

Figure 3:
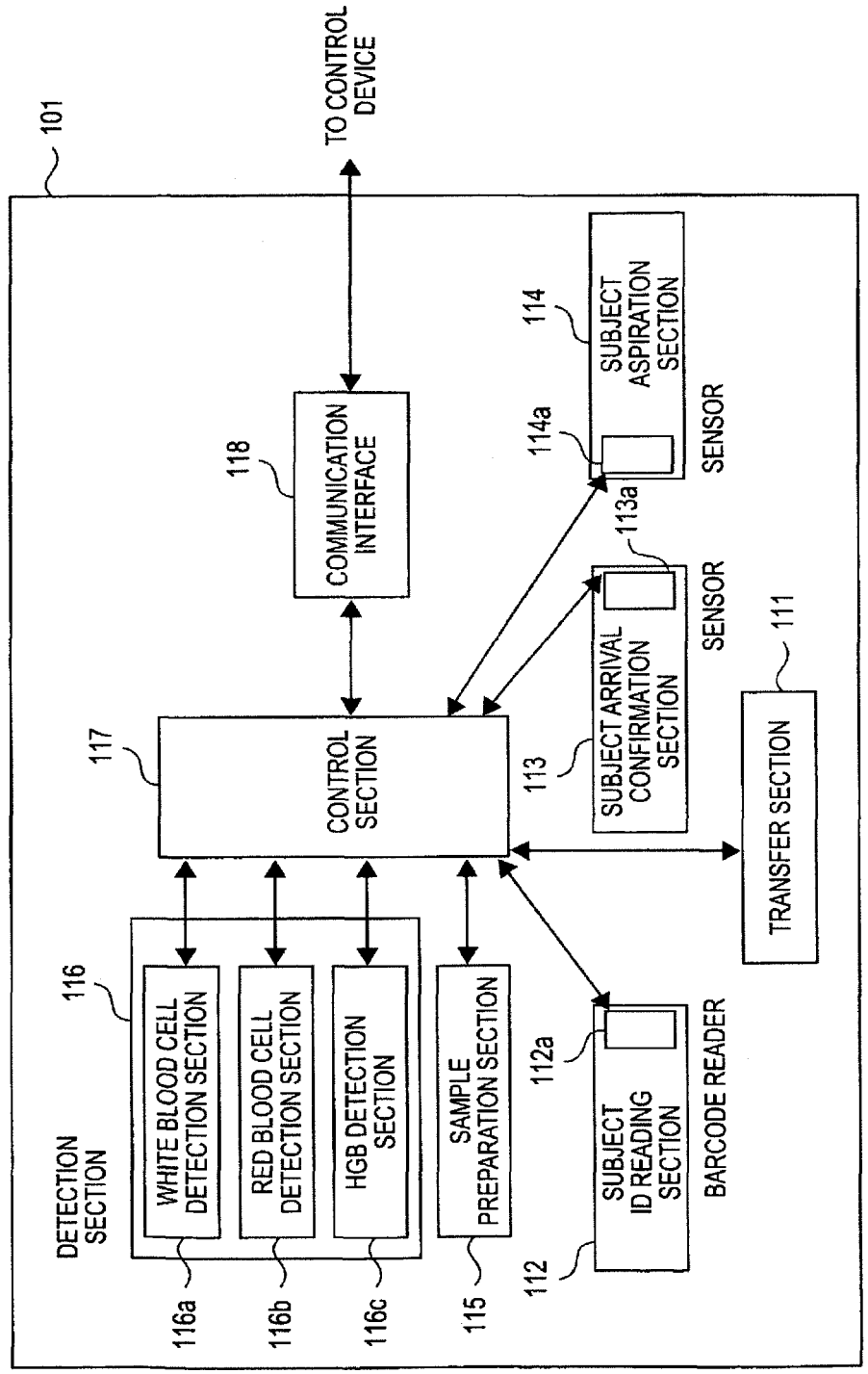
FIG. 3 is a block diagram illustrating a configuration of a main body of the analysis device illustrated in FIG. 1.

FIG. 3 is a block diagram of the analysis device main body 101.

The analysis device main body 101 is provided with the transfer section 111, a subject ID reading section 112, a subject arrival confirmation section 113, a subject aspiration section 114, a sample preparation section 115, a detection section 116, a control section 117, and a communication interface 118.

The subject ID reading section 112 is provided with a bar code reader 112a. Moreover, the subject arrival confirmation section 113 and the subject aspiration section 114 are provided with sensors 113a and 114a, respectively. Furthermore, the detection section 116 is provided with a white blood cell detection section 116a, a red blood cell detection section 116b, and an HGB detection section 116c.

The transfer section 111 is configured to be capable of transferring the subject to the subject ID reading section 112 and the subject aspiration section 114. The subject ID reading section 112 is configured such that a bar code attached on the subject transferred by the transfer section 111 is read by the bar code reader 112a, and the transfer section 111 transfers the subject to the subject aspiration section 114 after the bar code of the subject has been read by the bar code reader 112a. When the arrival of the subject on the subject aspiration section 114 has been confirmed by the sensor 113a of the subject arrival confirmation section 113, the subject aspiration section 114 performs an aspiration of the subject.

The subject aspiration section 114 is configured to monitor whether or not a predetermined amount of the subject has been aspirated by means of the sensor 114a. The subject aspirated in the subject aspiration section 114 is mixed with a measurement reagent in the sample preparation section 115, and measurement data are obtained by the respective detection sections of the detection section 116. The measurement data include measurement data of a white blood cell count obtained by the white blood cell detection section 116a, measurement data of a red blood cell count obtained by the red blood cell detection section 116b, and measurement data of a hemoglobin amount in blood obtained by the HUB detection section 116c. The control section 117 is configured to transmit the obtained measurement data to the control device 102 via the communication interface 118.

Figure 4:
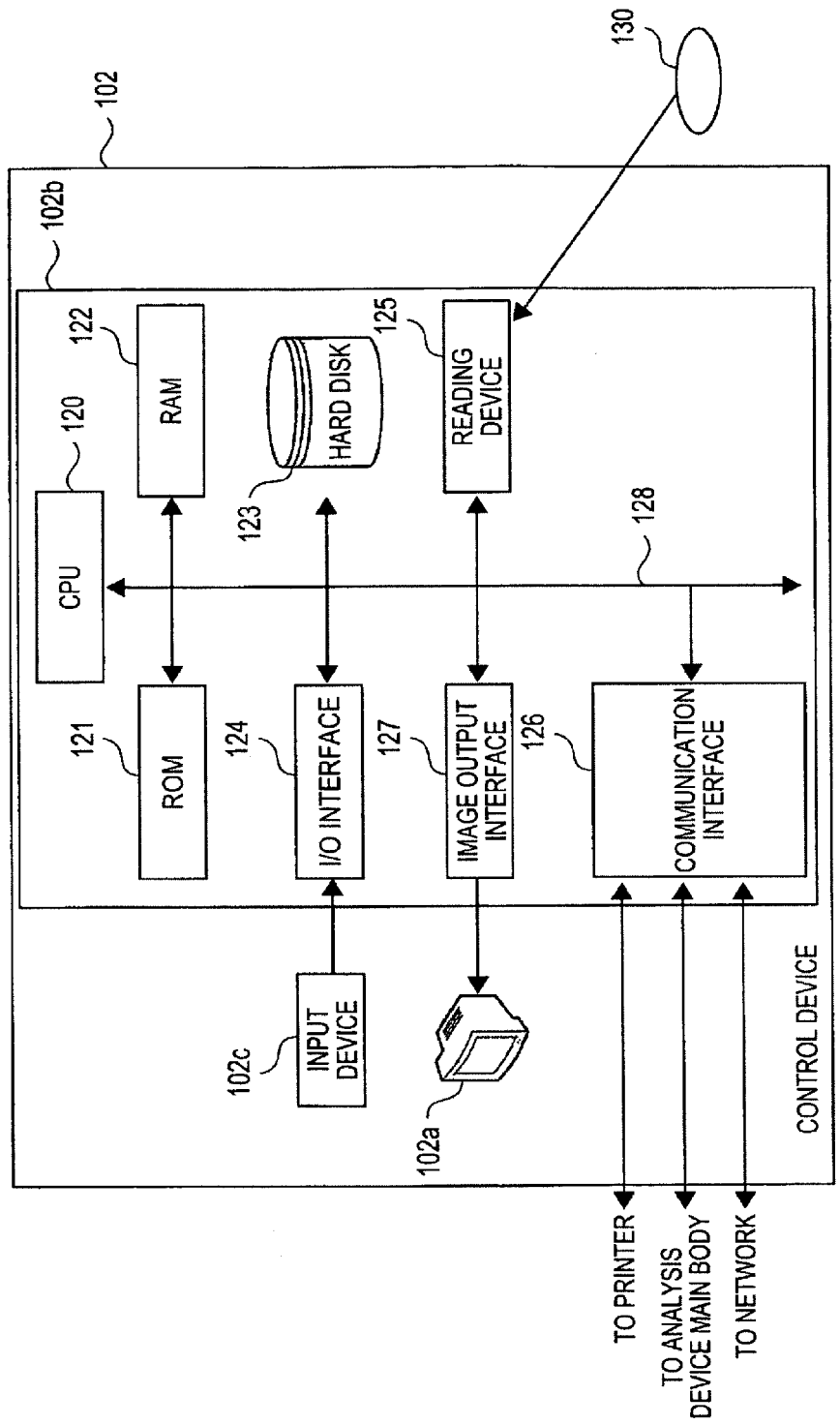
FIG. 4 is a hardware configuration diagram of a control device illustrated in FIG. 1.

FIG. 4 is a block diagram of the control device 102. As illustrated in FIG. 4, the control device 102 is a computer which is mainly configured by the display 102a, the main body 102b, and an input device 102c.

The main body 102b is mainly configured by a CPU 120, a ROM 121, a RAM 122, a hard disk 123, an I/O interface 124, a reading device 125, a communication interface 126, and an image output interface 127. The CPU 120, the ROM 121, the RAM 122, the hard disk 123, the I/O interface 124, the reading device 125, the communication interface 126, and the image output interface 127 are connected with each other via a bus 128 so as to be capable of performing data communication between them.

The CPU 120 is capable of executing a computer program stored in the ROM 121 and a computer program loaded to the RAM 122. When an application program is executed by the CPU 120, later-described functional blocks are realized, and thus a computer functions as the control device 102.

The ROM 121 is configured by a mask ROM, a PROM, an EPROM, an EEPROM, or the like, and stores therein a computer program executed by the CPU 120 and data used by the computer program.

The RAM 122 is configured by an SRAM, a DRAM, or the like. The RAM 122 is used for reading the computer program recorded on the ROM 121 and the hard disk 123. Moreover, the RAM 122 is used as a work area of the CPU 120 when the computer program is executed.

The hard disk 123 has installed therein a variety of computer programs to be executed by the CPU 120, such as an operating system or an application program, and data for use in execution of the computer programs.

The reading device 125 is configured by a flexible disk drive, a CD-ROM drive, a DVD-ROM drive, or the like. The reading device 125 is capable of reading the computer program or the data recorded on a portable recording medium 130.

The I/O interface 124 is configured by a serial interface such as a USB, an IEEE 1394, or an RS-232C, a parallel interface such as an SCSI, an IDE, or an IEEE 1284, an analog interface such as a D/A converter or an A/D converter, or the like. The I/O interface 124 has connected thereto the input device 102c that includes a keyboard and a mouse, so that data can be input to the main body 102b by an operator using the input device 102c.

The communication interface 126 is an Ethernet (the registered trademark) interface, for example, and the control device 102 is capable of transmitting or receiving data to or from the analysis device main body 101 connected thereto via the network 104 using a predetermined communication protocol by means of the communication interface 126.

The image output interface 127 is connected to the display 102a configured by an LCD, a CRT, or the like, and is configured to output an image signal corresponding to image data sent from the CPU 120 to the display 102a. The display 102a displays an image (screen) in accordance with the input image signal.

Figure 5:
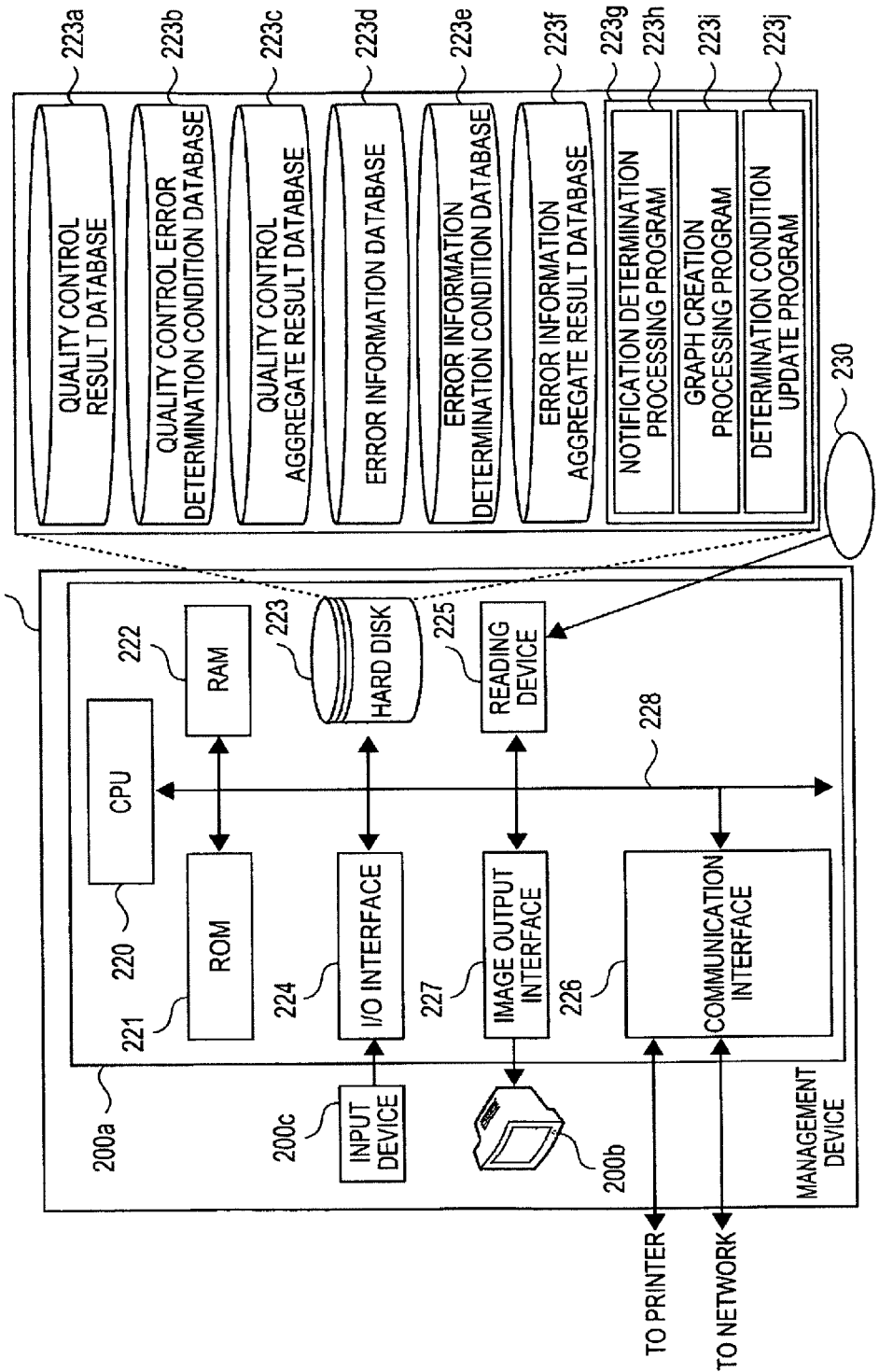
FIG. 5 is a hardware configuration diagram of a management device illustrated in FIG. 1.

FIG. 5 is a block diagram of the management device 200. The management device 200 is configured by a computer which is mainly configured by a main body 200a, a display 200b, and an input device 200c.

The main body 200a is mainly configured by a CPU 220, a ROM 221, a RAM 222, a hard disk 223, an I/O interface 224, a reading device 225, a communication interface 226, and an image output interface 227. The CPU 220, the ROM 221, the RAM 222, the hard disk 223, the I/O interface 224, the reading device 225, the communication interface 226, and the image output interface 227 are connected with each other via a bus 228 so as to be capable of performing data communication between them.

The CPU 220 is capable of executing a computer program stored in the ROM 221 and a computer program loaded to the RAM 222. When an application program is executed by the CPU 220, later-described functional blocks are realized, and thus a computer functions as the management device 201.

The ROM 221 is configured by a mask ROM, a PROM, an EPROM, an EEPROM, or the like, and stores therein a computer program executed by the CPU 220 and data used by the computer program.

The RAM 222 is configured by an SRAM, a DRAM, or the like. The RAM 222 is used for reading the computer program recorded on the ROM 221 and the hard disk 223. Moreover, the RAM 222 is used as a work area of the CPU 220 when the computer program is executed.

The hard disk 223 has installed therein a variety of computer programs to be executed by the CPU 220, such as an operating system or an application program, and data for use in execution of the computer programs.

The reading device 225 is configured by a flexible disk drive, a CD-ROM drive, a DVD-ROM drive, or the like. The reading device 225 is capable of reading the computer program or the data 230a recorded on a portable recording medium 230.

The application program does not only need to be provided by the portable recording medium 230 but also may be provided over an electronic telecommunication line (wired or wireless) from an external device communicably connected to a computer via the electronic telecommunication line. For example, the application program may be installed in a hard disk of a server computer on the Internet, so that the management device 200 makes an access to the server computer, downloads the computer program, and then installs the computer program in the hard disk 223.

Furthermore, an operating system capable of providing a graphical user interface, e.g., the Windows (the registered trademark) manufactured and sold by Microsoft Corporation (US), is installed in the hard disk 223. In the following description, the application program according to the present embodiment is assumed as running on the operating system.

In addition, the hard disk 223 stores, in a predetermined area thereof, a quality control result data database 223a, a quality control error determination condition database 223b, a quality control aggregate result database 223c, an error information database 223d, an error information determination condition database 223e, an error information aggregate result database 223f, and an application program 223g.

The application program 223g includes a notification determination processing program 223h, a graph creation processing program 223*i*, and a determination condition update program 223*j*. The quality control result data database 223*a* stores therein the quality control data received from the analysis device 100*a* and a determination result which has been determined as requiring a notification to a user based on a quality control error determination condition. The quality control error determination condition database 223*b* stores therein a determination condition for making a determination on the quality control data received from the analysis device 100*a* as to whether or not a notification to the user is required. The quality control aggregate result database 223*c* stores therein an output result of the graph creation processing program 223*i* with respect to the determination result stored in the quality control result database 223*a*. The error information database 223*d* stores therein the error information received from the management device 100 and a determination result which has been determined as requiring a notification to a user based on the error information determination condition. The error information determination condition database 223*e* stores therein a determination condition for making a determination on the error information received from the analysis device 100*a* as to whether or not a notification to the user is required.

The error information aggregate result 223*f* stores therein an output result of the graph creation processing program 223*i* with respect to the determination result stored in the error information database 223*d*. The notification determination processing program 223*h* is configured to make a determination on the quality control data and the error information received from the analysis device 100*a* as to whether a notification to a user is required. The graph creation processing program 223*i* is configured to create and output a graph of the determination results stored in the quality control result database 223*a* and the error information database 223*d*. The determination condition update program 223*j* is configured to update the error determination conditions stored in the quality control error determination condition database 223*b* and the error information determination condition database 223*e*.

The I/O interface 224 is configured by a serial interface such as a USB, an IEEE 1394, or an RS-232C, a parallel interface such as an SCSI, an IDE, or an IEEE 1284, an analog interface such as a D/A converter or an A/D converter, or the like. The I/O interface 224 has connected thereto the input device 200*c* that includes a keyboard and a mouse, so that data can be input to the main body 200*a* by an operator using the input device 200*c*.

The communication interface 226 is an Ethernet (the registered trademark) interface, for example, and the management device 200 is capable of transmitting or receiving data to or from the analysis device 100*a* connected thereto via the network 103 using a predetermined communication protocol and the terminal equipment of the call center connected thereto via the network 201, by means of the communication interface 226.

The image output interface 227 is connected to the display 200*b* configured by an LCD, a CRT, or the like, and is configured to output an image signal corresponding to image data sent from the CPU 220 to the display 200*b*. The display 200*b* displays an image (screen) in accordance with the input image signal.

Figure 6:
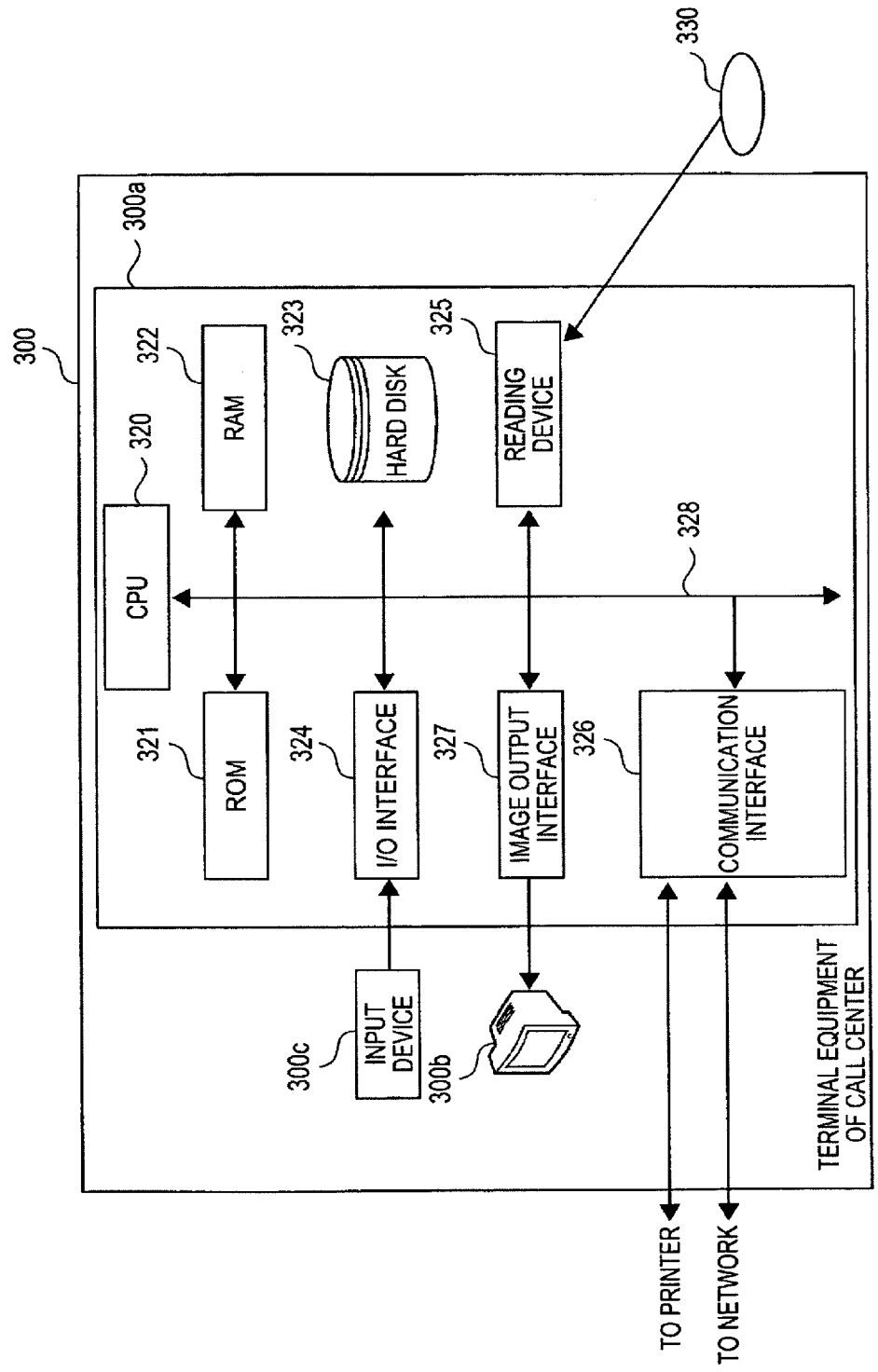
FIG. 6 is a hardware configuration diagram of a terminal equipment of a call center illustrated in FIG. 1.

FIG. 6 is a block diagram of the terminal equipment 300 of the call center 203. The terminal equipment 300 of the call center 203 is a computer which is mainly configured by a main body 300*a*, a display 300*b*, and an input device 300*c*.

The main body 300*a* is provided with a CPU 320, a ROM 321, a RAM 322, a hard disk 323, an I/O interface 324, a reading device 325, a communication interface 326, and an image output interface 327. The CPU 320, the ROM 321, the RAM 322, the hard disk 323, the I/O interface 324, the reading device 325, the communication interface 326, and the image output interface 327 are connected with each other via a bus 328 so as to be capable of performing data communication between them.

The CPU 320 is capable of executing a computer program stored in the ROM 321 and a computer program loaded to the RAM 322. When an application program is executed by the CPU 320, later-described functional blocks are realized, and thus a computer functions as the terminal equipment 300 of the call center 203.

The ROM 321 is configured by a mask ROM, a PROM, an EPROM, an EEPROM, or the like, and stores therein a computer program executed by the CPU 320 and data used by the computer program.

The RAM 322 is configured by an SRAM, a DRAM, or the like. The RAM 322 is used for reading the computer program recorded on the ROM 321 and the hard disk 323. Moreover, the RAM 322 is used as a work area of the CPU 320 when the computer program is executed.

The hard disk 323 has installed therein a variety of computer programs to be executed by the CPU 320, such as an operating system or an application program, and data for use in execution of the computer programs.

The reading device 325 is configured by a flexible disk drive, a CD-ROM drive, a DVD-ROM drive, or the like. The reading device 325 is capable of reading the computer program or the data 330*a* recorded on a portable recording medium 330.

The I/O interface 324 is configured by a serial interface such as a USB, an IEEE 1394, or an RS-232C, a parallel interface such as an SCSI, an IDE, or an IEEE 1284, an analog interface such as a D/A converter or an A/D converter, or the like. The I/O interface 324 has connected thereto the input device 300*c* that includes a keyboard and a mouse, so that data can be input to the main body 300*a* by an operator using the input device 300*c*.

The communication interface 326 is an Ethernet (the registered trademark) interface, for example, and the terminal equipment 300 of the call center 203 is capable of transmitting or receiving data to or from the management device 200 connected thereto via the network 201 using a predetermined communication protocol by means of the communication interface 326.

The image output interface 327 is connected to the display 300*b* configured by an LCD, a CRT, or the like, and is configured to output an image signal corresponding to image data sent from the CPU 320 to the display 300*b*. The display 300*b* displays an image (screen) in accordance with the input image signal.

Figure 7:
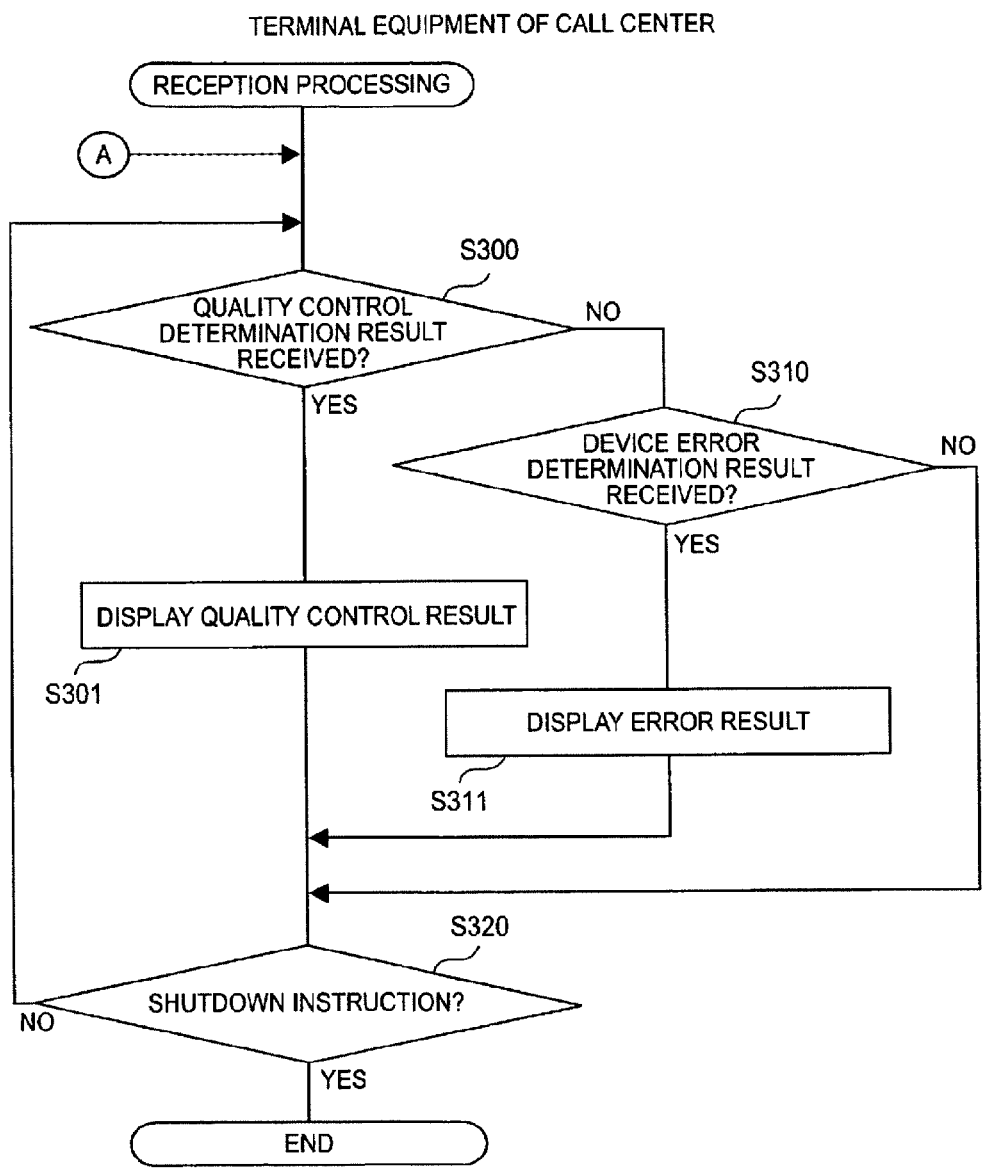
FIG. 7 is a flow chart illustrating an exemplary procedure of a main process performed by the management system illustrated in FIG. 1.

FIG. 7 is a flow chart illustrating the processing executed by the CPUs 120, 220 and 320 of the control device, the management device, and the terminal equipment. As illustrated in FIG. 7, the CPU 120 executes processing of making a determination in step S100 as to whether or not an error has occurred in the analysis device main body 101, i.e., whether or not the error information has been received from the analysis device main body 101.

In the analysis device main body 101, when the control section 117 has determined that it was impossible to read the bar code by means of the bar code reader 112*a*, the control section 117 transmits information representing a bar code read error to the control device 102. Moreover, when the control section 117 has determined that it was impossible to detect the arrival of the subject by means of the sensor 113*a*, in spite of a fact that the subject has actually been arrived, the control section 117 transmits error information representing a subject arrival confirmation error to the control device 102. Furthermore, when the control section 117 has determined that it was impossible to detect the aspiration of the subject by means of the sensor 114a, in spite of a fact that the subject has actually been aspirated, the control section 117 transmits error information representing a subject aspiration error to the control device 102.

When an error is determined to have occurred in step S100 (No in step S100), the CPU 120 stores therein the received error information (step S105). On the other hand, when the error is determined not to have occurred in step S100 (Yes in step S100), the CPU 120 makes a determination in step S101 as to whether or not the measurement data of the quality control substance 106 have been received from the analysis device main body 101.

The analysis device main body 101 is configured such that upon measurement of the quality control substance 106, the measurement data are transmitted from the detection section 117 to the control section 117 and the control section 117 transmits the measurement data to the control device 102.

When the measurement data are determined to have been received in step S101 (Yes in step S101), the CPU 120 analyzes the measurement data to acquire the quality control data 240 in step S102. Then, the CPU 120 stores in step S103 the quality control data 240 acquired in step S102 in the hard disk 123 and transmits in step S104 the quality control data 240 to the management device 200.

FIG. 8 illustrates the quality control data 240 transmitted in step S104 from the control device 102 to the management device 200. The quality control data 240 include device information 241, information 242 on the quality control substance 106, a quality control measurement date 243, and a quality control measurement result 244.

The device information 241 includes a facility name 241a being the name of a facility in which the analysis device is installed, a device name 241b, a PS Code 241c appended to each analysis device main body 101 at the time of factory shipment, and a serial number 241d.

The information 242 on the quality control substance 106 includes a quality control substance name 242a, a level 242b and a lot number 242c of the quality control substance 106, which are read from the bar code appended to the quality control substance 106 by means of a handy bar code reader or input by the input device 102c of the control device 102.

The quality control substance name 242a is information representing a name of the quality control substance 106. The level 242b is information representing a concentration, e.g., LOW, NORMAL, and the like, of the quality control substance 106. The lot number 242c is information representing a lot at the time of manufacture of the quality control substance 106.

The quality control measurement date 243 is information representing a date 243a and a time 243b of the receipt of the measurement data in step S101.

The quality control measurement result 244 is information representing the number of quality control measurement items 244a and a measurement result of each item. For example, in FIG. 8, the number of quality control measurement items 244a shows that there are three measurement items including an RBC 244b, an HGB 244c, and a WBC 244d. Moreover, the measurement result of each item shows that 4,470,000 cells/µL is for RBC, 13.5 g/L is for HGB, and 384 cells/µL is for WBC.

When the data received from the analysis device 100a via the networks 103 and 201 are determined to be the quality control data 240 in step S200 (Yes in step S200), the CPU 220 of the management device 200 stores the received quality control data 240 in an area of the quality control result database 223a of the hard disk 223 in step S201. Then, the CPU 220 activates the notification determination processing program 223h to make a determination on the quality control data 240 received from the analysis device 100a as to whether or not a notification is to be sent to a user of the analysis device 100a by referring to a user determination availability 255 of the quality control error determination condition 250, stored in the quality control error determination condition database 223b in step S202.

FIG. 9 is a schematic view illustrating the quality control error determination condition 250 stored in the quality control error determination condition database 223b. The quality control error determination condition 250 includes a material name 251 for identifying the quality control substance 106, a level 252, a measurement item 253, an abnormality determination rule 254, a user determination availability 255, and an external cooperative error determination availability 256.

The material name 251 is information representing a name of the quality control substance 106. The level 251 is information representing a concentration, e.g., LOW, NORMAL, and the like, of the quality control substance 106. The measurement item 253 is information representing a quality control measurement item. The abnormality determination rule 254 is information representing a determination item that makes a determination as to whether or not a notification to a user is required. For example, an action limit over 254a determines that a notification to the user is required when the quality control data 240 obtained from a plurality of analysis devices 100a have exceeded a value corresponding to an average thereof±an allowable percentage. A trend 254b determines that a notification to the user is required when the quality control data 240 have exceeded an allowable range and showed four consecutive ascending or descending tendencies in the same direction. The user determination availability 255 is a setting that is set by the user of the analysis device 100a, and is information representing whether or not a determination is to be made based on each abnormality determination rule 254 upon receipt of the quality control data 240.

The external cooperative error determination availability 256 is a setting that is set by the engineer 205 of the customer support center 202, and is information representing whether or not a determination is made based on each abnormality determination rule 254 upon receipt of the quality control data 240.

Thereafter, in step S203, the CPU 220 makes a determination on the quality control data 240 as to whether the notification to the user is to be sent by referring to the external cooperative error determination availability 256 of the quality control error determination condition 250.

In the present embodiment, a description has been made for a configuration in which a determination is made in step S202 as to whether or not a notification is to be sent to the user of the analysis device 100a by referring to the user determination availability 255, and thereafter, a determination is made in step S203 as to whether a notification is to be sent to the user of the analysis device 100a by referring to the external cooperative error determination availability 256. However, a configuration may be employed in which either one of the determination conditions may be selected so that a determination is made as to whether the notification is to be sent to the user of the analysis device 100a by referring to the selected determination condition.

When the CPU 220 has determined in step S220 that the notification to the user is required in the determination process of steps S202 or S203 (Yes in step S220), the CPU 220 stores the quality control result 260 (see FIG. 11) in the quality control result database 223a of the hard disk 223 in step S221, determines the terminal equipment 300 to be a destination of the notification from a plurality of terminal equipments 300 of the call center 203, and sends a notification, in step S223, that it is necessary to send a notification to the user of the terminal equipment 300 of the call center 203 via the network 201 by referring to the notification destination determined in step S222. On the other hand, when the CPU 220 has determined in step S220 that the notification to the user is not required (No in step S220), the processes of steps S221 to S223 are not performed and the flow proceeds to the step S230.

FIG. 11 is a schematic view illustrating the quality control result 260 sent from the CPU 220 of the management device 200 to the terminal equipment 300 of the call center 203 in step S223. The quality control result 260 includes device information 261, quality control substance information 262, a measurement item 263, a user determination condition 264, an engineer determination condition 265, a quality control measurement date 266, a quality control result 267, and an error name 268.

The device information 261 includes a device name 261b, a PS Code 261c appended to each analysis device main body 101 at the time of factory shipment, and a serial number 261d.

The quality control substance information 262 includes a quality control substance name 262a, a level 262b and a lot number 262c of the quality control substance 106.

The quality control substance name 262a is information representing a name of the quality control substance 106. The level 262b is information representing a concentration, e.g., LOW, NORMAL, and the like, of the quality control substance 106. The lot number 262c is information representing a lot at the time of manufacture. The measurement item 263 is information representing a quality control measurement item for the quality control data 240 received by the CPU 220, which have been determined by the notification determination processing program 223h as requiring the notification to the user. The user determination condition 264 and the engineer determination condition 265 are information representing the availability of each determination condition. The quality control measurement date 266 is information representing the date and time of completion of the quality control measurement. The quality control result 267 and the error name 268 are information representing the measurement result of the measurement item 263, which has been determined to be abnormal, and the abnormality determination rule 254, which has been determined as requiring the notification to the user, in the notification determination process of step S202 or S203.

Next, when the CPU 320 of the terminal equipment 300 of the call center 203 has determined in step S300 that the data received from the management device 200 via the network 201 are the quality control result 260 as illustrated in FIG. 11 (Yes in step S300), the CPU 320 displays the quality control result 260 as illustrated in FIG. 11 on the display 300b via the image output interface 327 in step S301, thereby informing that a notification to a user is required.

Thereafter, a determination is made in step S320 by the CPU 320 as to whether it has been instructed to shut down the operating system (OS) by the selection of shutdown from a start menu of the Windows (the registered trademark) being the OS of the terminal equipment 300 of the call center 203. When it has been determined in step S320 that the OS shutdown instruction has not been received (No in step S320), the flow returns to step S300. On the other hand, when it has been determined in step S320 that the OS shutdown instruction has been received (Yes in step S320), the flow proceeds to step S321, where the process is terminated by the CPU 320 shutting down the Windows (the registered trademark) being the OS of the terminal equipment 300 of the call center 203.

On the other hand, when the data have been determined in step S300 not to be the quality control result 260 as illustrated in FIG. 11 (No in step S300), the process of step S310 is performed.

Next, a description of the processes which are performed when the error information 280 has been transmitted from the analysis device 100a to the management device 200 via the networks 103 and 201, and thereafter, a notification is sent from the management device 200 to the terminal equipment 300 of the call center 203 via the network 201 will be provided with reference to FIG. 7.

When it has been determined in step S106 that a shutdown instruction has been sent to the analysis device main body 101 from a user thereof (Yes in step S106), the CPU 120 transmits the error information 280 as illustrated in FIG. 15 to the management device 200 via the networks 103 and 201 in step S107.

On the other hand, when it has been determined in step S106 that the shutdown instruction has not been sent to the analysis device main body 101 (No in step S106), the CPU 120 returns its flow to step S100 and the processes of steps S100 to S105 are repeated.

FIG. 15 is a schematic view illustrating the error information 280 transmitted from the analysis device 100a to the management device 200. The error information 280 sent from the analysis device 100a includes a serial number 281, device information 282, an error occurrence date and time 283, and an error code 284. The device information 282 is provided in order to identify the analysis device 100a and includes a facility name 282a being the name of a facility in which the analysis device 100a is installed, a name 282b of the analysis device 100a, a PS Code 282c appended to each analysis device main body at the time of factory shipment, and a serial number 282d. The error occurrence date and time 283 includes an error occurrence date 283a and an error occurrence time 283b. The error code 284 represents identification information of an error occurred, so that a type of the error received from the analysis device 100a can be uniquely identified.

When the CPU 220 of the management device 200 has determined in step S211 that the data received from the analysis device 100a via the networks 103 and 201 are the error information 280 as illustrated in FIG. 15 (Yes in step S211), the CPU 220 stores the received error information 280 in the error information database 223d of the hard disk 223 in step S212. Then, the CPU 220 executes the notification determination processing program 223h in step S213 to make a determination as to whether or not a notification is to be sent to the user of the analysis device 100a by referring to the error information determination condition 290 of the error information determination condition database 223e as illustrated in FIG. 16.

FIG. 16 is a schematic view of the error information determination condition 290 stored in the error information determination condition database 223e. The error information determination condition 290 includes a device name 291, an error name 292, an error code 293, and an action limit 294. The device name 291 is information representing a name of the analysis device 100a. The error name 292 is information representing a name of the error. The error code 293 is information representing identification information uniquely corresponding to the error name 292. The action limit 294 is information representing the limit of the number of times the error as specified in the error code 293 is allowed to occur per one day, the information being used in such a way that the notification to the user is determined to be necessary when the error information 280 received from the analysis device 100a showed the number of occurrences of the error has exceeded the number as specified in the action limit 294.

A description will be provided by way of example in which the error name 292 of the error information determination condition 290 illustrated in FIG. 16 is a short sample error. The short sample error represents an error occurring when it is determined that the sensor 114a was impossible to sufficiently aspirate a subject, in spite of a fact that the control section 117 is aspirating the subject. When the error has occurred 10 times or more per one day, it is determined that the notification to the user is required.

When the notification determination processing program 223h executed in step S213 has determined in step S220 that the notification to the user is required (Yes in step S220), the error information determination result 295 as illustrated in FIG. 17 is stored in the error information database 223d of the hard disk 223 in step S221. Then, the terminal equipment 300 of the call center 203, which will be a notification destination, is determined in step S222, and a notification that the notification to the user is to be required is sent in step S223 to the terminal equipment 300 of the call center 203 via the network 201 by referring to the notification destination determined in step S222.

On the other hand, when the notification to the user has been determined not to be necessary in step S220 (No in step S220), the CPU 220 determines whether or not a predetermined period has been elapsed in step S230, while the processes of steps S221 to S223 are not executed.

FIG. 17 is a schematic view illustrating the error information determination result 295 sent from the management device 200 to the terminal equipment 300 of the call center 203.

The error information determination result 295 sent from the management device 200 to the terminal equipment 300 of the call center 203 includes device information 296, an error occurrence date and time 297, error information 298, and an action limit 299. The device information 296 includes a facility name 296a being the name of a facility in which the analysis device 100a is installed, a name 296b of the analysis device 100a, a PS Code 296c appended to each analysis device main body at the time of factory shipment, and a serial number 296d, for identification of the analysis device 100a. The error occurrence date and time 297 includes information representing the date and time of occurrence of an error. The error information 298 includes an error name 298a and an error code 298b. The error name 298a is information representing a name of an error occurring in the analysis device 100a. The error code 298b is information representing identification information of an error corresponding to the error name.

The action limit 299 is information representing the limit of the number of times the error as specified by the error information 298 is allowed to occur per one day, the information being used in such a way that the notification to the user is determined to be necessary when the error information 298 showed the number of occurrences of the error has exceeded the number as specified in the action limit 299.

Next, when the CPU 320 of the terminal equipment 300 of the call center 203 has determined in step S310 that the data received from the management device 200 via the network 201 are the error information determination result 295 as illustrated in FIG. 17 (Yes in step S310), the CPU 320 displays the error information determination result 295 as illustrated in FIG. 17 on the display 300b via the image output interface 327 in step S311.

On the other hand, when the data have been determined not to be the error information determination result 295 as illustrated in FIG. 17 (No in step S310), the CPU 320 executes the process of step S320.

Thereafter, a determination is made in step S320 by the CPU 320 as to whether it has been instructed to shut down the operating system (OS) by the selection of shutdown from a start menu of the Windows (the registered trademark) being the OS of the terminal equipment 300 of the call center 203. When it has been determined in step S320 that the OS shutdown instruction has not been received (No in step S320), the flow returns to step S300. On the other hand, when it has been determined in step S320 that the OS shutdown instruction has been received (Yes in step S320), the flow proceeds to step S321, where the process is terminated by the CPU 320 shutting down the Windows (the registered trademark) being the OS of the terminal equipment 300 of the call center 203.

Moreover, when the CPU 220 has determined in step S230 that a predetermined period (e.g., one month) has been elapsed after previous graph creation processing (Yes in step S230), the CPU 220 executes the graph creation processing program 223i illustrated in FIG. 5 in step S231 to collect the quality control result 260 stored in the quality control result database 223a and the error information determination result 295 stored in the error information database 223d to be output to a predetermined area of the hard disk 223. After execution of the graph creation processing (step S231), the flow returns to step S200.

On the other hand, when the CPU 220 has determined in step S230 that the predetermined period has not been elapsed (No in step S230), the flow proceeds to step S232.

Next, when there is an update request to update any one of the user determination availability 255, the external cooperative error determination availability 256 of the quality control error determination condition 250 illustrated in FIG. 9 and the action limit 294 of the error information determination condition 290 from the engineer 205 of the customer support center 202 in step S232 (Yes in step S232), the CPU 220 executes the determination condition update program 223j in step S233 to update the determination condition stored in the quality control error determination condition database 223b or the error information determination condition database 223e of the hard disk 223 as illustrated in FIG. 5 based on the received determination condition.

FIG. 10 is a schematic view of a screen on which the engineer 205 of the customer support center 202 performs the update of the quality control error determination condition database 223b illustrated in FIG. 5.

A quality control error determination condition setting dialog 310 mainly includes a material name 311, a level 312, a measurement item 313, an abnormality determination rule 314, user determination availability 315, external cooperative error determination availability 316, an OK button 317, and a Cancel button 318.

The material name 311 is information representing a name of the quality control substance 106. The level 312 is information representing a concentration, e.g., LOW, NORMAL, and the like, of the quality control substance 106. The measurement item 313 is information representing a quality control measurement item. The abnormality determination rule 314 is information representing a determination item that makes a determination as to whether or not a notification to a user is required. The user determination availability 315 is a setting that is set by the user of the analysis device 100a, and includes a user determination availability check box 315*a*. The user determination availability check box 315*a* is information representing that a determination as to the necessity of sending the notification to the user is to be performed when the box is checked (selected) while the determination as to the necessity of sending the notification to the user is not to be performed when the box is not checked. The external cooperative error determination availability 316 is a setting that is set by the engineer 205 of the customer support center 202, and includes an external cooperative error determination availability check box 316*a*. The external cooperative error determination availability check box 316*a* is information representing that a determination as to the necessity of sending the notification to the user is to be performed when the box is checked (selected) while the determination as to the necessity of sending the notification to the user is not to be performed when the box is not checked.

When the OK button 317 is pressed, the contents of the quality control error determination condition database 223*b* are updated to the setting contents being displayed on the quality control error determination condition setting dialog 310, and the quality control error determination condition setting dialog 310 is closed. When the Cancel button 318 is pressed, the contents of the quality control error determination condition database 223*b* are not updated, and the quality control error determination condition setting dialog 310 is closed.

For example, the quality control error determination condition setting dialog 310 illustrated in FIG. 10 shows that for a material having settings wherein the material name 311 is quality control substance A, the level 312 is LOW, the measurement item 313 is RBC, and the abnormality determination rule 314 is action limit over, when the quality control data 240 have been received from the analysis device 100*a*, the determination as to the necessity of the notification to the user is performed in step S202, while the determination as to the necessity of the notification to the user is not performed in step S203.

On the other hand, when the CPU 220 has determined in step S232 that there is no update request for any of the user determination availability 255 and the external cooperative error determination availability 256 of the quality control error determination condition 250 illustrated in FIG. 9 and the action limit 294 of the error information determination condition 290 illustrated in FIG. 16 (No in step S232), the flow returns to step S200.

FIG. 12 is a flow chart illustrating a procedure of the graph creation processing in step S231. The CPU 220 acquires the quality control result 260 for a predetermined period from the quality control result database 223*a* in step S271 and then classifies the quality control result 260 for each device name 261*b* from the acquired result in step S272.

Next, in step S273, the quality control result 260 is classified for each quality control substance name 262*a* from the quality control result 260 classified in step S272, and the quality control result 260 is further classified for each level 262*b* representing the concentration of the quality control substance 106. Furthermore, the classified quality control result 260 is classified for each measurement item 263 in step S274, and the classified quality control result 260 is further classified for each error name 268 in step S275.

In this way, a plurality of groups is generated: e.g., a group (Group 1) wherein a target period is from a previous graph creation date to a present graph creation date, the analysis device name is device A, the quality control substance name is quality control substance A, the level is LOW, the measurement item is RBC, and the error name is action limit over; a group (Group 2) wherein a target period is from a previous graph creation date to a present graph creation date, the analysis device name is device A, the quality control substance name is quality control substance A, the level is LOW, the measurement item is RBC, and the error name is trend; a group (Group 3) wherein a target period is from a previous graph creation date to a present graph creation date, the analysis device name is device A, the quality control substance name is quality control substance B, the level is NORMAL, the measurement item is HGB, and the error name is action limit over; and the like.

Thereafter, in step S276, a notification determination rate is calculated for each of the groups generated in step S275 by using the following formula (1).

$$\text{Notification Determination Rate} = \text{(Number of Notifications to User)}/\text{(Total Number of Quality Control Data)} \quad (1)$$

Herein, the number of notifications to user corresponds to the number of quality control results 260 contained in each of the groups. Moreover, the total number of quality control data corresponds to the number of quality control data 240 for each level of the quality control substance received from the plurality of analysis devices 100*a* during the target period.

For example, when the notification determination rate for each of the groups is calculated, in calculation of the notification determination rate of Groups 1 and 2, the total number of quality control data represents the number of quality control data 240 contained in a group wherein the target period is from the previous graph creation date to the present graph creation date, the analysis device name is device A, the quality control substance name is quality control substance A, and the level is LOW. Moreover, in calculation of the notification determination rate of Group 3, the total number of quality control data represents the number of quality control data 240 contained in a group wherein the target period is from the previous graph creation date to the present graph creation date, the analysis device name is device A, the quality control substance name is quality control substance B, and the level is NORMAL.

In step S277, the notification determination rate calculated in step S276 is output as an accumulated bar graph for each measurement item 263. Furthermore, in step S278, the graph output in step S277 is stored in a predetermined area of the quality control aggregate result database 223*c*.

Figure 13:
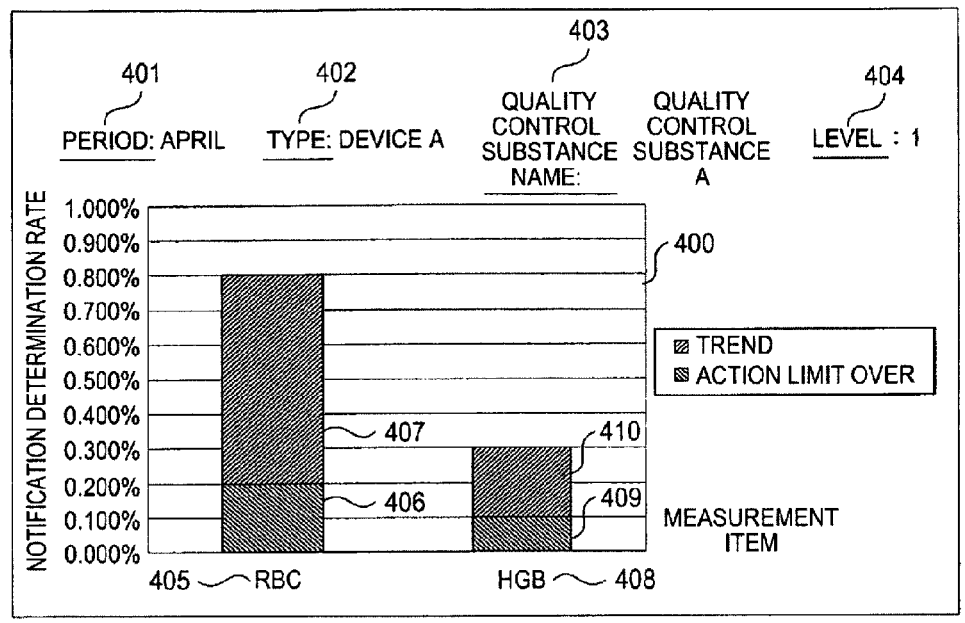
FIG. 13 is a diagram illustrating an example of a graph that is output in step S277 and displayed on the terminal equipment 300 of the call center 203.

FIG. 13 is an example of a graph output in step S277 and displayed to the terminal equipment 300 of the call center 203. On an upper portion of the graph, an aggregate period 401, an analysis device name 402, a quality control substance name 403, and a quality control substance level 404 are displayed.

In a graph portion 400, an accumulated bar graph showing the notification determination rate for each item of the abnormality determination rule 254 of the quality control data 240 is displayed. Herein, RBC 405 is information representing a quality control measurement item. Reference numeral 406 is information representing the notification determination rate of the action limit of the RBC 405. Reference numeral 407 is information representing the notification determination rate of the trend of the RBC 405. Moreover, HGB 408 is information representing a quality control measurement item. Reference numeral 409 is information representing the notification determination rate of the action limit of the HGB 408. Reference numeral 410 is information representing the notification determination rate of the trend of the HGB 408.

As will be understood from the quality control measurement aggregate result for device A on April illustrated in FIG.

13, for the quality control substance A having a concentration level of 1, the quality control item RBC shows a high notification determination rate based on the trend compared with the HGB. For example, when the high notification determination rate results from poor storage stability of the RBC of the quality control substance A, the quality control substance 106 itself has a problem but the analysis device 100a does not have any problem. Therefore, it can be determined that the determination condition on the trend of the RBC is to be loosened to decrease the number of notifications to the user.

Next, the CPU 220 acquires the error information determination result 295 for a predetermined period from the error information database 223d of the hard disk 223 in step S281 and then classifies the error information determination result 295 for each name 296b of the analysis device 100a from the acquired error information determination result 295 in step S282. Subsequently, in step S283, the error information determination result 295 is classified for each error information 298 from the error information determination result 295 classified in step S282.

In this way, a plurality of groups is generated: e.g., a group (Group 4) wherein a target period is from a previous graph creation date to a present graph creation date, the analysis device name is device A, and the error name is short sample; a group (Group 5) wherein a target period is from a previous graph creation date to a present graph creation date, the analysis device name is device A, and the error name is whole blood aspiration motor stoppage abnormality; a group (Group 6) wherein a target period is from a previous graph creation date to a present graph creation date, the analysis device name is device B, and the error name is short sample; and the like.

Thereafter, in step S284, a notification determination rate is calculated for each of the groups generated in step S283 by using the following formula (2).

Notification Determination Rate=(Number of Determinations as Requiring Notification)/(Total Number of Device Names 296b being Connected to Management Device 200)    (2)

Herein, the number of determinations as requiring notification corresponds to the number of error information determination results 295 contained in each of the groups. Moreover, the total number of device names 296b being connected to the management device 200 corresponds to the number of analysis devices 100a having the same device name, being connected to the management device 200.

For example, when the notification determination rate for each of the groups is calculated, in calculation of the notification determination rate of Groups 4 and 5, the total number of device names 296b being connected to the management device 200 represents the number of analysis devices 100a having the analysis device name of device A among the analysis devices 100a being connected to the management device 200. Moreover, in calculation of the notification determination rate of Group 6, the total number of device names 296b being connected to the management device 200 represents the number of analysis devices 100a having the analysis device name of device B among the analysis devices 100a being connected to the management device 200.

Figure 14:
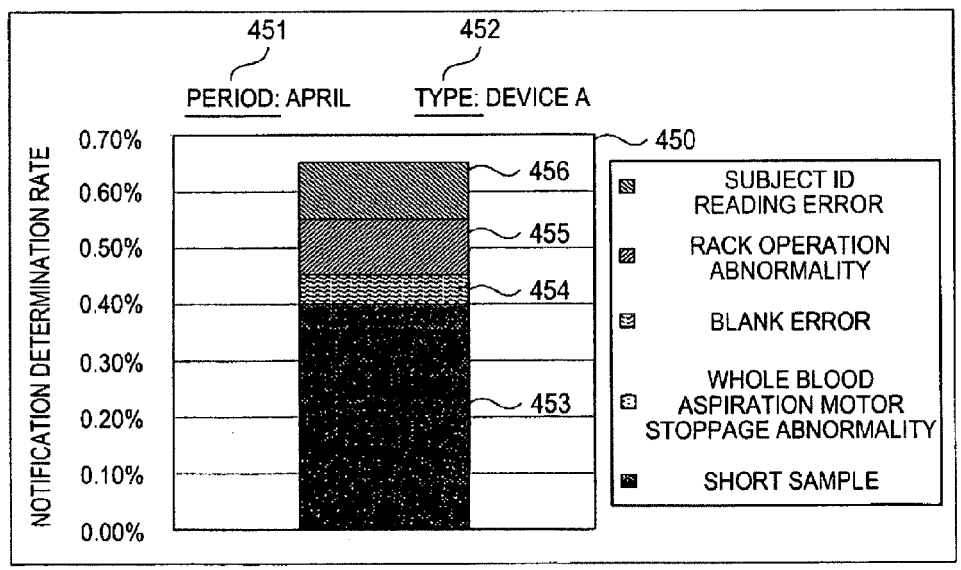
FIG. 14 is a diagram illustrating an example of a graph that is output in step S285 and displayed on the terminal equipment 300 of the call center 203.

In step S285, the notification determination rate calculated in step S284 is output as an accumulated bar graph for each device name 296b. Furthermore, in step S286, the graph output in step S285 is stored in a predetermined area of the error information aggregate result database 223E FIG. 14 is an example of a graph output in step S285 and displayed to the terminal equipment 300 of the call center 203. On an upper portion of the graph, an aggregate period 451 and an analysis device name 452 are displayed.

Reference numeral 453 is information representing the notification determination rate of a short sample error. The short sample error represents an error occurring when the subject aspiration section 114 has detected that the sensor 114a was impossible to sufficiently aspirate a subject at the time of the subject aspiration.

Reference numeral 454 is information representing the notification determination rate of a blank error. The blank error represents an error occurring when the detection section 116 has detected that the sample of a previous subject is left in the detection section 116 by a predetermined concentration or more.

Reference numeral 455 is information representing the notification determination rate of a rack operation abnormality error. The rack operation abnormality error is an error occurring when the transfer section 111 was unable to normally transfer a subject to the subject ID reading section 112 or the subject aspiration section 114.

Moreover, reference numeral 456 is information representing the notification determination rate of a subject ID reading error. The subject ID reading error is an error occurring when it was impossible to read a bar code appended to the subject by means of the bar code reader 112a.

It can, therefore, be expected from FIG. 14, showing the notification determination rate of an error (rack operation abnormality) related to the transfer section 111 being 0.1 percent, that for example, when the notification determination rate is increasing compared with a previous month, the frequency of occurrence of the error related to the transfer section 111 will increase with time. Therefore, in order to reduce a shutdown time of the analysis device 100a on next months, it is necessary to decrease the setting value of the action limit 294 for the rack operation abnormality of the error information determination condition 290 for the error related to the transfer section 111 and dispatch the engineer 204 to a facility being determined as requiring a notification, thereby preventing serious failures.

Moreover, when it is determined that notifications have been frequently sent to the user of the analysis device 100a in which the short sample error has occurred due to a reason other than a failure of the device, such as a reason that the amount of a subject filled in a test tube is smaller than a prescribed amount, it may be determined that it is necessary to increase the setting value of the action limit 294 for the short sample of the error information determination condition 290, thereby decreasing the number of notifications to the user.

Furthermore, since it is possible to obtain information on which unit showed a high error occurrence frequency, it is possible to know which unit preferentially requires an improvement design in future device development, which becomes useful information in development of an efficient device capable of reducing a shutdown time of the analysis device 100a.

In the embodiment described above, a description has been made for a configuration in which when the quality control data 240 and the error information 280 received from the analysis device 100a have been determined as requiring a notification to a user, the management device 200 of the customer support center 202 sends a notification thereof to the terminal equipment 300 of the call center 203. However, the present invention is not limited to this and the terminal equipment 300 of the call center 203 may not be provided, for example. In such a case, a configuration may be employed in which when the notification to the user is determined to be necessary, the management device 200 sends a notification thereof to the control device 102. This notification may be sent in such a way that a method of coping with the occurred error is sent via an email. Owing to such a configuration, it is possible to send a notification of occurrence of a trouble to a user even in the absence of the engineer 204 of the call center 203 to thereby eliminate further processing in the call center 203, and thus, the trouble can be promptly notified to the user of the analysis device 100a.

Moreover, in the present embodiment, a description has been made for a configuration in which when the management device 200 of the customer support center 202 has received the error information 280, the received error information 280 is stored in the error information database 223d of the hard disk 223 in step S212 of the flow chart illustrated in FIG. 7, and the notification determination processing program 223h is executed in step S213 to make a determination as to whether or not the notification to the user is required. However, a configuration may be employed in which the CPU 220 does not execute the determination processing of step S213.

That is, when the CPU 220 of the management device 200 has determined in step S211 that the data received from the analysis device 100a via the networks 103 and 201 are the error information 280 as illustrated in FIG. 15 (Yes in step S211), the CPU 220 stores the received error information 280 in the error information database 223d of the hard disk 223 in step S212.

Next, when the CPU 220 has determined in step S230 that a predetermined period (e.g., one month) has been elapsed after previous graph creation processing (Yes in step S230), the CPU 220 executes the graph creation processing program 223i illustrated in FIG. 5 in step S231.

Then, the CPU 220 acquires the error information 280 for a predetermined period from the error information database 223d of the hard disk 223 in step S281 and classifies the error information 280 for each name 282b of the analysis device 100a from the acquired error information 280 in step S282. Subsequently, in step S283, the error information 280 is classified for each error code 284 from the error information 280 classified in step S282.

In this way, a plurality of groups is generated: e.g., a group (Group 7) wherein a target period is from a previous graph creation date to a present graph creation date, the analysis device name is device A, and the error name is short sample; a group (Group 8) wherein a target period is from a previous graph creation date to a present graph creation date, the analysis device name is device A, and the error name is whole blood aspiration motor stoppage abnormality; a group (Group 9) wherein a target period is from a previous graph creation date to a present graph creation date, the analysis device name is device B, and the error name is short sample; and the like.

Thereafter, in step S284, an abnormality occurrence rate is calculated for each of the groups generated in step S283 by using the following formula (3).

Abnormality Occurrence Rate=(Number of Errors Received from Analysis Device 100a)/(Total Number of Device Names 296b being Connected to Management Device 200)  (3)

Herein, the number of errors received from the analysis device 100a corresponds to the number of error codes 284 contained in each of the groups.

Moreover, the total number of device names 296b being connected to the management device 200 corresponds to the number of analysis devices 100a having the same device name, being connected to the management device 200.

For example, when the abnormality occurrence rate for each of the groups is calculated, in calculation of the abnormality occurrence rate of Groups 7 and 8, the total number of device names 296b being connected to the management device 200 represents the number of analysis devices 100a having the analysis device name of device A among the analysis devices 100a being connected to the management device 200. Moreover, in calculation of the abnormality occurrence rate of Group 9, the total number of device names 296b being connected to the management device 200 represents the number of analysis devices 100a having the analysis device name of device B among the analysis devices 100a being connected to the management device 200.

In step S285, the abnormality occurrence rate calculated in step S284 is output as an accumulated bar graph for each device name 296b. Furthermore, in step S286, the graph output in step S285 is stored in a predetermined area of the error information aggregate result database 223f.

FIG. 18 is an example of a graph output in step S285 and displayed to the terminal equipment 300 of the call center 203. On an upper portion of the graph, an aggregate period 461 and an analysis device name 462 are displayed. Reference numeral 463 is information representing the abnormality occurrence rate of a short sample error. Reference numeral 464 is information representing the abnormality occurrence rate of a blank error. Reference numeral 465 is information representing the abnormality occurrence rate of a rack operation abnormality error. Reference numeral 466 is information representing the abnormality occurrence rate of a subject ID reading error. Owing to such a configuration, since it is possible to identify an error showing a high occurrence frequency for each analysis device, it is possible to know which unit preferentially requires an improvement design in future device development, which becomes useful information in development of an efficient device capable of reducing a shutdown time of the analysis device 100a.

Moreover, in the present embodiment, a description has been made for a configuration in which the engineer 205 of the customer support center 202 performs the update of the quality control error determination condition database 223b. However, a configuration may be employed in which the user 107 of the analysis device 100a performs the update of the quality control error determination condition database 223b. For example, in response to a request sent from the analysis device 100a to the management device 200, an analysis device-side quality control error determination condition setting dialog 350, as illustrated in FIG. 19, for updating the quality control error determination condition database 223b may be displayed on the display 102a of the control device 102.

The analysis device-side quality control error determination condition setting dialog 350 mainly includes a user determination condition setting grid 351, an OK button 357, and a Cancel button 358.

The user determination condition setting grid 351 includes a material name 352, a level 353, a measurement item 354, an abnormality determination rule 355, and user determination availability 356. The material name 352 is information representing a name of the quality control substance 106. The level 353 is information representing a concentration, e.g., LOW, NORMAL, and the like, of the quality control substance 106. The measurement item 354 is information representing a quality control measurement item. The abnormality determination rule 355 is information representing a determination item that makes a determination as to whether or not a notification to a user is required. The user determination availability 356 is a setting that is set by the user of the analysis device 100a, and includes a user determination availability check box 356a. The user determination availability check box 356a is information representing that a determination as to the necessity of sending the notification to the user is to be performed when the box is checked (selected) while the determination as to the necessity of sending the notification to the user is not to be performed when the box is not checked. When the OK button 357 is pressed, the contents of the quality control error determination condition database 223b are updated to the setting contents being displayed on the quality control error determination condition setting dialog 350, and the quality control error determination condition setting dialog 350 is closed. When the Cancel button 358 is pressed, the contents of the quality control error determination condition database 223b are not updated, and the quality control error determination condition setting dialog 350 is closed.

For example, the analysis device-side quality control error determination condition setting dialog 350 illustrated in FIG. 19 shows that for a material having settings wherein the material name 352 is quality control substance A, the level 353 is LOW, the measurement item 354 is RBC, and the abnormality determination rule 355 is action limit over or trend, when the management device 200 has received the quality control data 240 from the analysis device 100a, the determination as to the necessity of the notification to the user is performed by the CPU 220 of the management device 200 in step S202. Meanwhile, for a material having settings wherein the material name 352 is quality control substance A, the level 353 is NORMAL, the measurement item 354 is HGB, and the abnormality determination rule 355 is action limit over, the determination as to the necessity of the notification to the user is not performed in step S202.

In addition, a description has been made for a configuration in which the analysis device-side quality control error determination condition setting dialog 350 in FIG. 19 selects the availability of each abnormality determination rule 355. For example, when the quality control data 240 received from the analysis device 100a have exceeded an average±an allowable percentage of the quality control data 240 obtained from the plurality of analysis devices 100a, the action limit over 355a determines that the notification to the user is required. However, a configuration may be employed in which the allowable percentage may be changed: that is, the settings of the abnormality determination rule 355 may be changed.

Furthermore, in the present embodiment, a description has been made for a configuration in which when the notification to the user has been determined to be necessary in the determination processing on the quality control data 240 received from the analysis device 100a, the terminal equipment 300 of the call center 203 is determined as the notification destination in step S222. However, a configuration may be employed in which the analysis device 100a is determined as the notification destination when the user determination availability 255 shows that the notification to the user is required, while the terminal equipment 300 of the call center 203 is determined as the notification destination when the external cooperative error determination availability 256 shows that the notification to the user is required.

Furthermore, in the present embodiment, a description has been made for a configuration in which the CPU 220 executes the graph creation processing of step S231 when a predetermined period has been elapsed from the completion of the previous graph creation processing of step S230. However, a configuration may be employed in which the CPU 220 executes the graph creation processing of step S231 when the engineer 205 of the customer support center 202 has instructed to execute the graph creation processing program 223i.

What is claimed is:

1. A management device connected to an analyzer and a terminal equipment via a network, the analyzer installed in a first facility and the terminal equipment installed in a second facility different from the first facility, the management device comprising:
 a data receiving unit that receives quality control data which is obtained by measuring a quality control substance from the analyzer;
 a memory that stores a plurality of abnormality determination rules, each abnormality determination rule being provided to determine whether or not a notification of abnormality is required for the quality control data received by the data receiving unit, each abnormality determination rule being associated with a plurality of availability settings, each availability setting being provided to determine whether or not the notification of abnormality for the abnormality determination rule is to be sent; and
 a processor operatively connected to the data receiving unit and the memory, the processor being configured to:
  receive selection of one or more availability settings for at least one abnormality determination rule,
  determine whether or not a respective notification of abnormality associated with the at least one abnormality determination rule is required for the quality control data received by the data receiving unit based on the one or more availability settings selected for the at least one abnormality determination rule,
  when determined that the respective notification of abnormality is required, select at least one of the analyzer and the terminal equipment as a notification destination for the respective notification of abnormality based on the one or more availability settings selected for the at least one abnormality determination rule, and
  send the respective notification of abnormality to the notification destination when determined that the respective notification of abnormality is required.

2. The management device according to claim 1, wherein selection of the analyzer as the notification destination is based on an availability setting selected via the network from the analyzer.

3. The management device according to claim 1, wherein selection of the terminal equipment as the notification destination is based on an availability setting selected from the management device.

4. The management device according to claim 1, wherein the quality control substance is a sample prepared using blood.

5. The management device according to claim 1, wherein the at least one abnormality determination rule determines to make the respective notification when the quality control data received from the analyzer exceeds an allowable range from an average value of the quality control data obtained from a plurality of analyzers.

6. The management device according to claim 1, wherein the at least one abnormality determination rule determines to make the respective notification when the quality control data received from the analyzer deviates from an allowable range continuously for a predetermined number of times in a same direction.

7. The management device according to claim 1, which is installed in the second facility.

8. The management device according to claim 1, wherein the second facility is a facility of a vendor who provides a maintenance service for the analyzer.

9. The management device according to claim 8, wherein the terminal equipment is installed in a call center in the facility of the vendor who provides the maintenance service.

10. The management device according to claim 1, further comprising:
an aggregate result generator that generates an aggregate result, in which the number of notifications or notification rate, at which the notification of the abnormality is made based on an abnormality determination rule, is aggregated for each abnormality determination rule for the plurality of quality control data received by the data receiving unit; and
an display that outputs the aggregate result generated by the aggregate result generator.

11. The management device according to claim 10, wherein the display outputs the number of notifications or the notification rate, at which the notification of the abnormality is made, as an accumulated bar graph for each abnormality determination rule.

12. The management device according to claim 1, wherein the quality control data which is obtained by measuring a quality control substance from the analyzer includes measurement results for a plurality of measurement items associated with the quality control substance and the memory stores a plurality of the abnormality determination rules for each measurement item.

13. A management system comprising: the management device; the analyzer; and the terminal equipment according to claim 1.

14. A quality control method of an analyzer by a management device connected to the analyzer and a terminal equipment via a network, the analyzer installed in a first facility and the terminal equipment installed in a second facility different from the first facility, the quality control method comprising the following steps executed by the management device:
receiving quality control data obtained by measuring a quality control substance by the analyzer via the network,
reading an abnormality determination rule for determining whether or not a notification of abnormality is required for the quality control data from a memory storing a plurality of the abnormality determination rules, the abnormality determination rule being associated with a plurality of availability settings for determining whether or not the notification of abnormality is to be sent,
receiving selection of one or more availability settings for the abnormality determination rule,
determining whether or not the notification of the abnormality is required for the received quality control data based on the one or more availability settings selected for the abnormality determination rule,
when the notification of abnormality is required, selecting at least one of the analyzer and the terminal equipment as a notification destination for the notification of abnormality based on the one or more availability settings selected for the abnormality determination rule, and
sending a notification of the abnormality to the notification destination via the network when the notification of the abnormality is required.

15. The quality control method of an analyzer according to claim 14, wherein the analyzer is selected as a notification destination based on an availability setting whose selection is received via the network from the analyzer.

16. The quality control method of an analyzer according to claim 14, wherein the terminal equipment is selected as a notification destination based on an availability setting whose selection is received from the management device.

17. The quality control method of an analyzer according to claim 14, wherein the quality control substance is a sample prepared using blood.

18. The quality control method of an analyzer according to claim 14, wherein the abnormality determination rule determines to make the notification when the quality control data received from the analyzer exceeds an allowable range from an average value of the quality control data obtained from a plurality of analyzers.

19. The quality control method of an analyzer according to claim 14, wherein the abnormality determination rule determines to make the notification when the quality control data received from the analyzer deviates from an allowable range continuously for a predetermined number of times in a same direction.

20. The quality control method of an analyzer according to claim 14, wherein the management device further executes:
generating an aggregate result, in which the number of notifications or notification rate, at which the notification of the abnormality is made based on a respective abnormality determination rule, is aggregated for each abnormality determination rule for the plurality of quality control data received by the data receiving unit; and
outputting the aggregate result on a display.

* * * * *